(12) United States Patent
Loccufier

(10) Patent No.: US 9,278,949 B2
(45) Date of Patent: Mar. 8, 2016

(54) POLYMERIZABLE THIOXANTHONES

(71) Applicant: AGFA GRAPHICS NV, Mortsel (BE)

(72) Inventor: Johan Loccufier, Mortsel (BE)

(73) Assignee: Agfa Graphics NV, Mortsel (BE)

( * ) Notice: Subject to any disclaimer, the term of this patent is extended or adjusted under 35 U.S.C. 154(b) by 0 days.

(21) Appl. No.: 14/404,955

(22) PCT Filed: Jul. 1, 2013

(86) PCT No.: PCT/EP2013/063836
§ 371 (c)(1),
(2) Date: Dec. 2, 2014

(87) PCT Pub. No.: WO2014/009194
PCT Pub. Date: Jan. 16, 2014

(65) Prior Publication Data
US 2015/0158839 A1    Jun. 11, 2015

(30) Foreign Application Priority Data

Jul. 10, 2012  (EP) .................................... 12175728

(51) Int. Cl.
| | |
|---|---|
| *C07D 335/16* | (2006.01) |
| *C08F 228/06* | (2006.01) |
| *C07D 335/10* | (2006.01) |
| *C07D 335/12* | (2006.01) |
| *C08F 220/26* | (2006.01) |
| *C08F 122/10* | (2006.01) |
| *C09D 11/101* | (2014.01) |
| *C09D 11/322* | (2014.01) |
| *C09D 11/40* | (2014.01) |

(52) U.S. Cl.
CPC ............ *C07D 335/16* (2013.01); *C07D 335/10* (2013.01); *C07D 335/12* (2013.01); *C08F 122/105* (2013.01); *C08F 220/26* (2013.01); *C08F 228/06* (2013.01); *C09D 11/101* (2013.01); *C09D 11/322* (2013.01); *C09D 11/40* (2013.01)

(58) Field of Classification Search
CPC ..................................................... C07D 335/16
See application file for complete search history.

(56) References Cited

FOREIGN PATENT DOCUMENTS

| | | |
|---|---|---|
| EP | 1 616 921 A1 | 1/2006 |
| EP | 2 161 264 A1 | 3/2010 |
| EP | 2 199 273 A1 | 6/2010 |
| EP | 2 246 330 A1 | 11/2010 |
| EP | 2 444 429 A1 | 4/2012 |
| GB | 2 454 579 A | 5/2009 |
| JP | 2004-224993 A | 8/2004 |
| WO | 03/033492 A1 | 4/2003 |

OTHER PUBLICATIONS

STN search (Dec. 9, 2015).*
Official Communication issued in International Patent Application No. PCT/EP2013/063836, mailed on Nov. 8, 2013.

* cited by examiner

*Primary Examiner* — Vu A Nguyen
(74) *Attorney, Agent, or Firm* — Keating & Bennett, LLP

(57) ABSTRACT

A polymerizable thioxanthone according to Formula (I):

$$A-O-\underset{R_1}{\underset{|}{\overset{R_2}{\overset{|}{C}}}}_n-\underset{O}{\underset{||}{C}}-\overset{H}{\underset{|}{N}}-R_3,\quad\text{Formula (I)}$$

wherein A represents a thioxanthone moiety; R1 and R2 are independently selected from the group consisting of a hydrogen, an alkyl group, an alkenyl group, an alkynyl group, an aryl group, and a heteroaryl group; n represents 1 or 2; and R3 represents a moiety including at least one free radical polymerizable group selected from the group consisting of an acrylate, a methacrylate, an acrylamide, a methacrylamide, a styrene group, a maleate, a fumarate, an itaconate, a vinyl ether, a vinyl ester, an allyl ether, and an allyl ester.

17 Claims, No Drawings

POLYMERIZABLE THIOXANTHONES

CROSS-REFERENCE TO RELATED APPLICATIONS

This application is a 371 National Stage Application of PCT/EP2013/063836, filed Jul. 1, 2013. This application claims the benefit of European Application No. 12175728.0, filed Jul. 10, 2012, which is incorporated by reference herein in its entirety.

BACKGROUND OF THE INVENTION

1. Field of the Invention

The present invention relates to specifically substituted polymerizable thioxanthones with high reactivity for LED exposure and increased thermal stability.

2. Description of the Related Art

Short run packaging printing is shifting from conventional printing techniques, such as offset printing, to digital printing, where inkjet is one of the preferred technologies. In inkjet printing, tiny drops of ink are projected directly onto an ink-receiver surface without physical contact between the printing device and the ink-receiver. The printing device stores the printing data electronically and controls a print head for ejecting the drops image-wise on an ink-receiver. Within ink jet for digital packaging printing, there is a clear evolution towards higher image quality and higher printing speeds in combination with LED curing. In order to satisfy these demands, a new print head design is required. These print heads require a specific ink design as they only can operate with very low viscous inks. The inks for high resolution, high speed short run digital packaging printing have to combine low viscosity, low migrating properties after curing and high sensitivity for LED exposure.

Polymeric photoinitiators are known to improve the low migrating properties after curing, but also to increase the viscosity. Even polymeric photoinitiators with a compact design, like the hyperbranched photoinitiators disclosed by EP 1616921 A (AGFA), increase the viscosity of radiation curable compositions too much for the new print head designs.

Polymerizable photoinitiators are also known to improve the low migrating properties after curing. For example, EP 2161264 A (AGFA) discloses polymerizable Norrish Type II photoinitiators having a benzophenone group or a thioxanthone group in inkjet inks that exhibit low extractable amounts of the photoinitiators and their residues after curing.

Thioxanthones suitable for low migration radiation curable compositions have also been disclosed in EP 2444429 A (AGFA), EP 2199273 A (AGFA), GB 2454579 (LAMBSON), WO 03/033492 A (COATES BROTHERS), JP 2004224993 A (NIPPON KAYAKU) and EP 2246330 A (SIEGWERK).

High sensitivity for UV-LED exposure, preferably 395 nm LED exposure, requires bathochromic photoinitiators. Thioxanthones are known as being particularly preferred photoinitiators for LED exposure.

However, it has been observed that in very low viscous radiation curable compositions, the type of polymerizable photoinitiator also influences the thermal stability and shelf life upon storage, especially when they exhibit improved curing speed. Fluctuations in viscosity have a large impact on the jetting performance and reliability of the new print heads operating with very low viscous inkjet inks.

Therefore, there is still a need for highly reactive photoinitiators, especially for LED curing, with an improved stability performance in radiation curable formulations.

SUMMARY OF THE INVENTION

In order to overcome the problems described above, preferred embodiments of the present invention provide a polymerizable thioxanthone as described below.

It was surprisingly found that by including an amido group in a specific position on the thioxanthone moiety that not only an improved curing speed, but also an improved thermal stability of the radiation curable composition was obtained. The improved curing speed can possibly be explained by the formation of an intramolecular hydrogen bond between the oxygen of the ether group in the thioxanthone ring and the hydrogen of the amido group. However, it is not understood why or how the thermal stability is improved.

Further advantages and benefits of the invention will become apparent from the description hereinafter.

DETAILED DESCRIPTION OF THE PREFERRED EMBODIMENTS

Definitions

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methylbutyl etc. The term "alkyl" includes an alkaryl group, i.e. an arylated alkyl group, wherein an aryl group is substituted for a hydrogen atom of the alkyl group. The alkyl group is, unless otherwise specified, preferably a substituted or unsubstituted alkyl group including 1 to 15 carbon atoms, but is preferably a $C_1$ to $C_6$-alkyl group or an alkaryl group. The aryl group in the alkaryl group is preferably a substituted or unsubstituted phenyl group.

The term "alkenyl" is, unless otherwise specified, preferably a substituted or unsubstituted alkenyl group including 1 to 15 carbon atoms, preferably a $C_1$ to $C_6$-alkenyl group.

The term "alkynyl" is, unless otherwise specified, a substituted or unsubstituted alkynyl group including 1 to 15 carbon atoms, more preferably a $C_1$ to $C_6$-alkynyl group.

The term "aryl" is, unless otherwise specified, preferably a substituted or unsubstituted aryl group including 6 to 15 carbon atoms, more preferably a phenyl group or a naphthyl group. The term "aryl" includes an aralkyl group which is an aryl group, preferably a phenyl group or naphthyl group, substituted preferably by one, two, three or more $C_1$ to $C_6$-alkyl groups.

The term "heteroaryl" is, unless otherwise specified, preferably a substituted or unsubstituted heteroaryl group including 6 to 15 carbon atoms, more preferably a five- or six-membered ring substituted by one, two or three oxygen atoms, nitrogen atoms, sulphur atoms, selenium atoms or combinations thereof.

The term "alkoxy" is, unless otherwise specified, preferably a substituted or unsubstituted alkoxygroup including 1 to 15 carbon atoms, more preferably a $C_1$ to $C_6$-alkoxygroup, and most preferably a methoxy or ethoxy group.

Unless otherwise specified a substituted alkyl group, a substituted alkenyl group, a substituted alkynyl group, a substituted aryl and a substituted heteroaryl group are preferably substituted by one or more substituents selected from the group consisting of methyl, ethyl, n-propyl, isopropyl, n-butyl, isobutyl and tertiary-butyl, methylester, ethylester, amide, methoxy, ethoxy, thioether, ketone, aldehyde, sulfoxide, sulfone, sulfonate ester, sulphonamide, —Cl, —Br, —I, —OH, —SH, —CN and —NO$_2$.

The term "monofunctional monomer" means a monomer having only one polymerizable group, for example an acrylate group.

The term "polyfunctional monomer" means a monomer having two, three or more polymerizable groups, e.g. two acrylate groups and one vinyl ether group.

Polymerizable Thioxanthones

The polymerizable thioxanthone according to a first aspect of the present invention is a compound according to Formula (I):

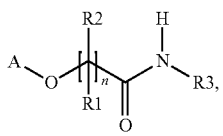

Formula (I)

wherein, A represents a thioxanthone moiety; R1 and R2 are independently selected from the group consisting of a hydrogen, an alkyl group, an alkenyl group, an alkynyl group, an aryl group and a heteroaryl group; n represent 1 or 2; and R3 represents a moiety comprising at least one free radical polymerizable group selected from the group consisting of an acrylate, a methacrylate, an acrylamide, a methacrylamide, a styrene group, a maleate, a fumarate, an itaconate, a vinyl ether, a vinyl ester, an allyl ether and an allyl ester.

In a preferred embodiment R1 and R2 are independently selected from the group consisting of hydrogen and a substituted or unsubstituted alkyl group.

In a more preferred embodiment, R1 and R2 are independently selected from the group consisting of hydrogen and an alkyl group having 1 to 6 carbon atoms, a hydrogen being particularly preferred. In a preferred embodiment, R1 and R2 are both hydrogen.

In a preferred embodiment, said free radical polymerizable group is selected from the group consisting of an acrylate and a methacrylate, an acrylate being particularly preferred.

In a preferred embodiment n is equal to 1.

In an even more preferred embodiment, the polymerizable thioxanthones according to the present invention include at least two free radical polymerizable groups selected from the group consisting of an acrylate, a methacrylate, an acrylamide, a methacrylamide, a styrene group, a maleate, a fumarate, an itaconate, a vinyl ether, a vinyl ester, an allyl ether and an allyl ester, an acrylate and a methacrylate being particularly preferred, an acrylate being the most preferred.

In a preferred embodiment, the polymerizable thioxanthone has a structure according to Formula (II) or Formula (III):

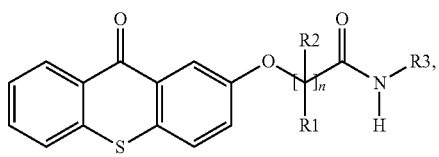

Formula (II)

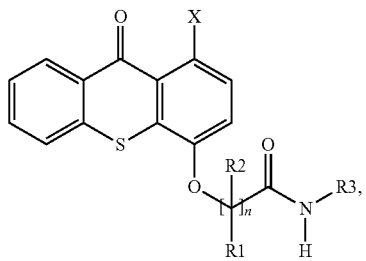

Formula (III)

wherein R1 to R3 have the same meaning as above for the polymerizable thioxanthone according to Formula (I); and X is selected from the group consisting of hydrogen, halogen, an alkyl group and an alkoxy group.

In a more preferred embodiment, X represents a halogen, chloride and fluoride being more preferred, fluoride being the most preferred.

In a preferred embodiment, the moiety R3 of the polymerizable thioxanthone includes two or three free radical polymerizable groups, preferably independently selected from the group consisting of an acrylate and a methacrylate, more preferably the two or three free radical polymerizable groups are an acrylate group.

The moiety R3 preferably contains no more than 4 to 80 carbon atoms, more preferably 7 to 60 carbon atoms, and most preferably 8 to 50 carbon atoms. Generally a lower viscosity can be obtained by having a smaller amount of carbon atoms in the moiety R3. The atoms linking the one, two, three or more free radical polymerizable groups to the amide group may all consist of carbon atoms or they may include one or more hetero atoms, preferably one or more oxygen atoms. In a preferred embodiment, the moiety R3 includes one or more ethyleneoxy or propyleneoxy groups.

All the above preferred embodiments mentioned above may be combined, for example, the polymerizable thioxanthone may have two or three acrylate groups, a value for n equal to 1, and R1 and R2 both representing a hydrogen.

Preferred examples of polymerizable thioxanthones according to the present invention are given by Table 1, without being limited thereto.

TABLE 1

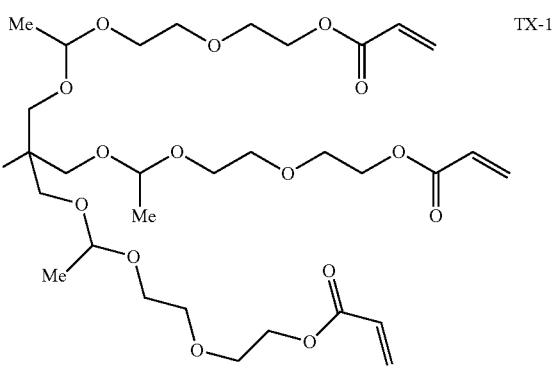

TX-1

TABLE 1-continued
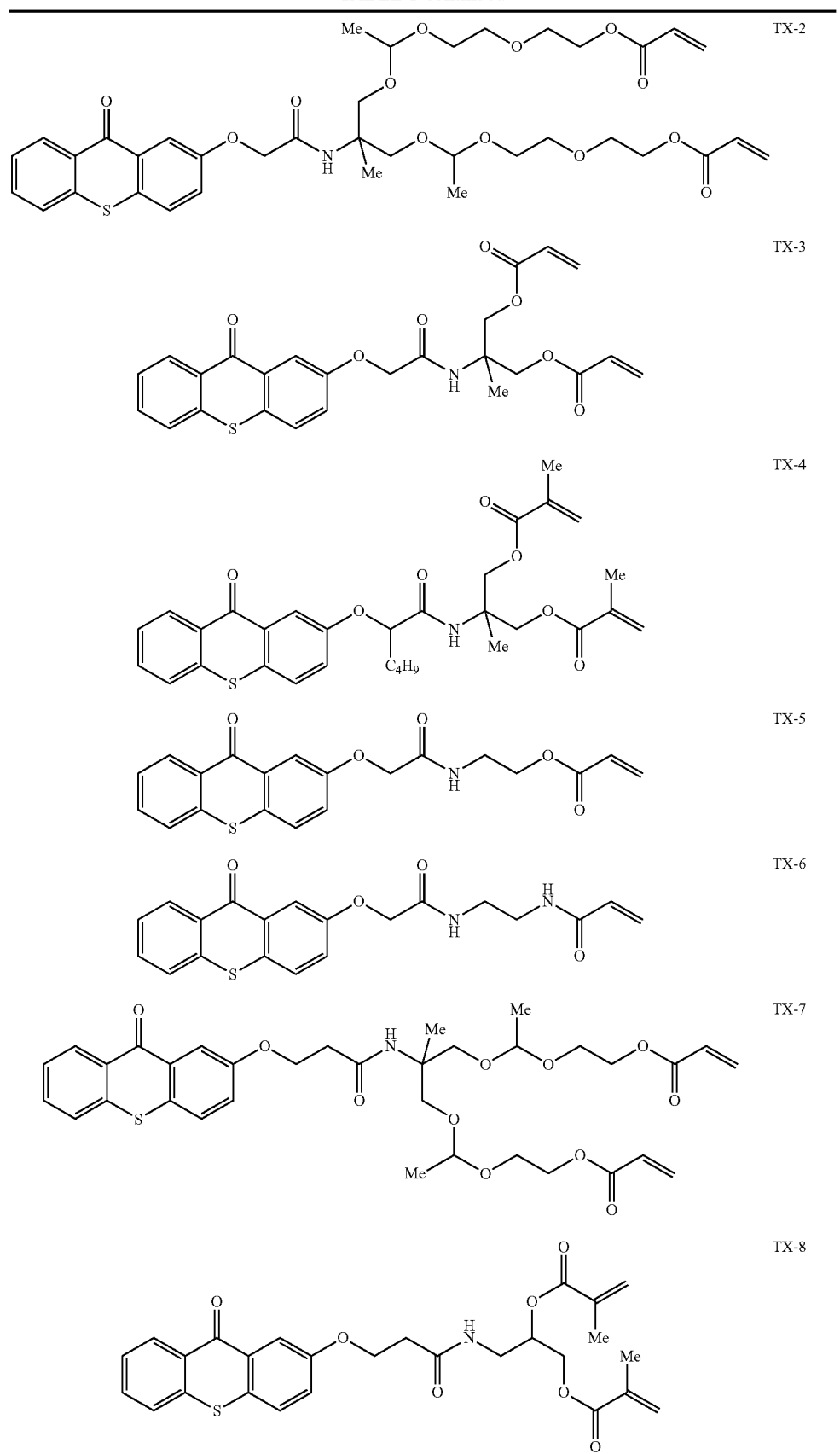

TABLE 1-continued
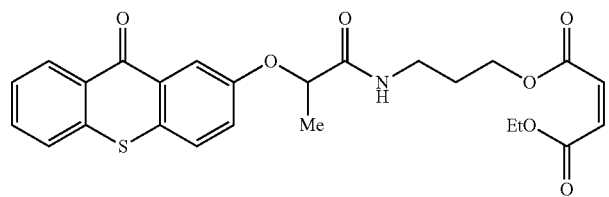 [SMILES: CCOC(=O)/C=C\C(=O)OCCCNC(=O)C(C)Oc1ccc2sc3ccccc3c(=O)c2c1] TX-9
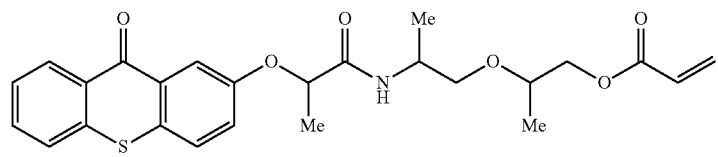 [SMILES: C=CC(=O)OCC(C)OCC(C)NC(=O)C(C)Oc1ccc2sc3ccccc3c(=O)c2c1] TX-10
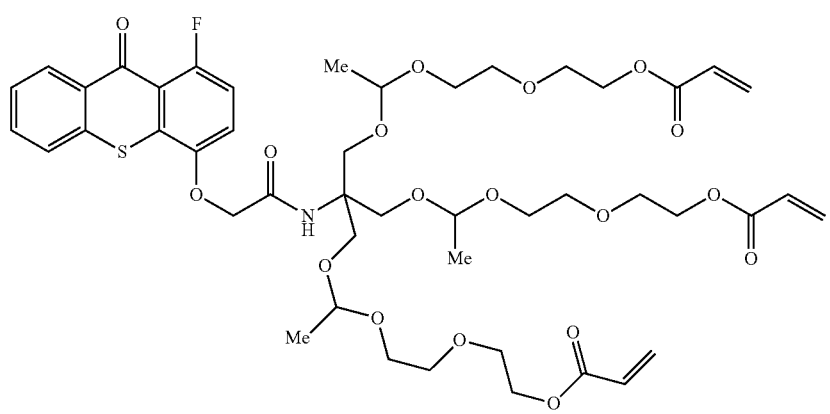 [SMILES: C=CC(=O)OCCOCCOC(C)OCC(COC(C)OCCOCCOC(=O)C=C)(COC(C)OCCOCCOC(=O)C=C)NC(=O)COc1ccc(F)c2c(=O)c3ccccc3sc12] TX-11
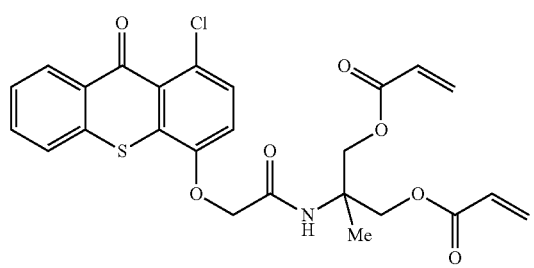 [SMILES: C=CC(=O)OCC(C)(COC(=O)C=C)NC(=O)COc1ccc(Cl)c2c(=O)c3ccccc3sc12] TX-12
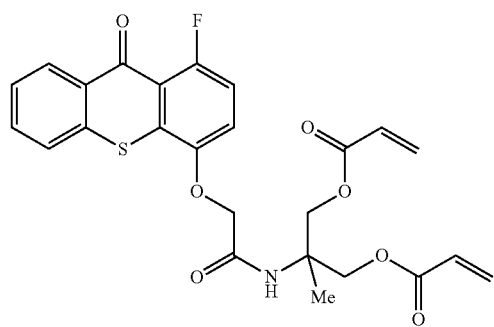 [SMILES: C=CC(=O)OCC(C)(COC(=O)C=C)NC(=O)COc1ccc(F)c2c(=O)c3ccccc3sc12] TX-13

TABLE 1-continued
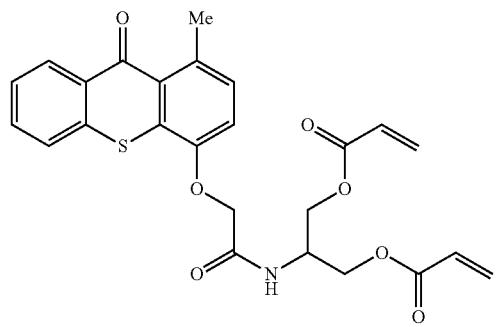 [SMILES: C=CC(=O)OCC(COC(=O)C=C)NC(=O)COc1ccc(C)c2c(=O)c3ccccc3sc12] TX-14
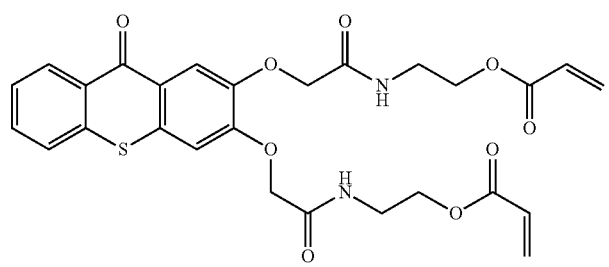 [SMILES: C=CC(=O)OCCNC(=O)COc1cc2sc3ccccc3c(=O)c2cc1OCC(=O)NCCOC(=O)C=C] TX-15
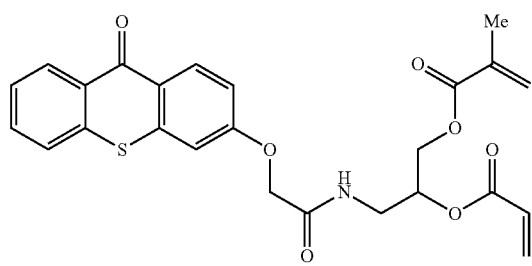 [SMILES: C=CC(=O)OC(CNC(=O)COc1ccc2c(=O)c3ccccc3sc2c1)COC(=O)C(=C)C] TX-16
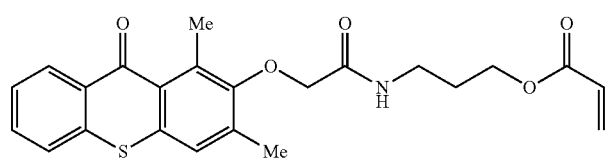 [SMILES: C=CC(=O)OCCCNC(=O)COc1c(C)cc2sc3ccccc3c(=O)c2c1C] TX-17
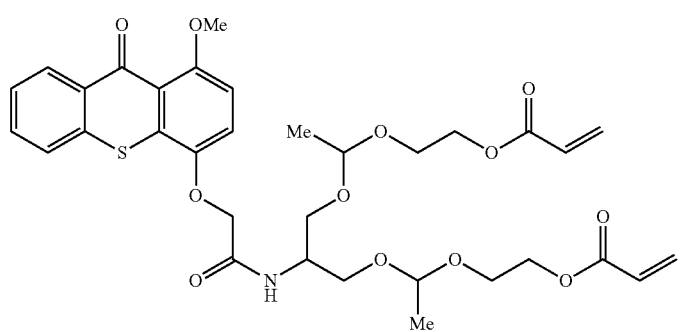 [SMILES: C=CC(=O)OCCOC(C)OCC(COC(C)OCCOC(=O)C=C)NC(=O)COc1ccc(OC)c2c(=O)c3ccccc3sc12] TX-18

TABLE 1-continued

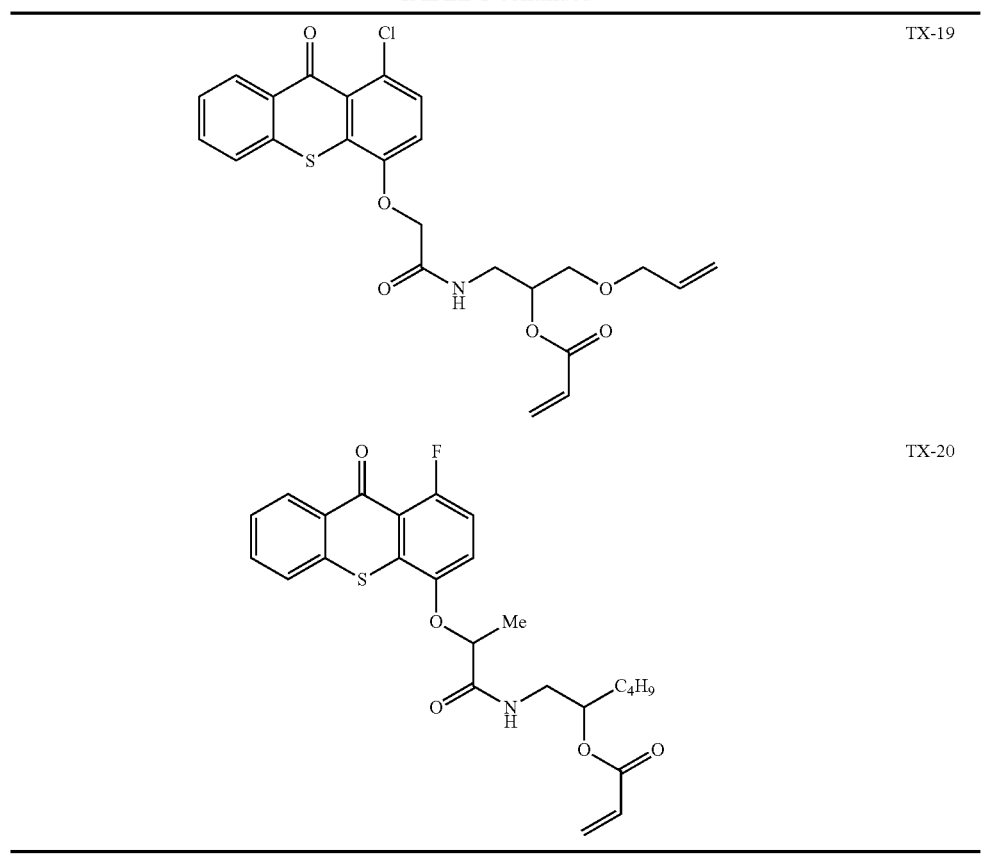

TX-19

TX-20

The polymerizable thioxanthones can be prepared by simple synthesis methods well-known to a person skilled in the art. For the sake of completeness, the preparation of some of the polymerizable thioxanthone photoinitiators has been exemplified in Example 1.

Radiation Curable Compositions

The polymerizable thioxanthone can be used in any radiation curable composition, but is advantageously used for preparing low viscous radiation curable compositions such as inkjet inks and flexographic inks.

In preferred embodiment, the radiation curable composition is an inkjet ink having a viscosity smaller than 15 mPa·s at 40° C. and at a shear rate of 1,000 s$^{-1}$.

The polymerizable thioxanthone can be advantageously used in radiation curable compositions to reduce the amount of extractables and volatiles after curing. This effect is especially observed for low viscous radiation curable compositions containing vinylether acrylate monomers and derivatives thereof.

In a preferred embodiment, the radiation curable composition includes a monomer according to Formula (IV):

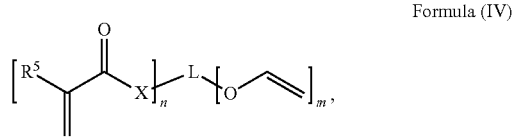

Formula (IV)

wherein, L represents a linking group; m and n independently represent an integer having a value from 1 to 5; X represents O, S or NR$^6$; and R$^5$ and R$^6$ independently represent hydrogen or a substituted or unsubstituted alkyl group; with the proviso that when X=NR$^6$ then L and R$^6$ may together form a ring system.

In a preferred embodiment, the monomer according to Formula (IV) has a structure according to Formula (V):

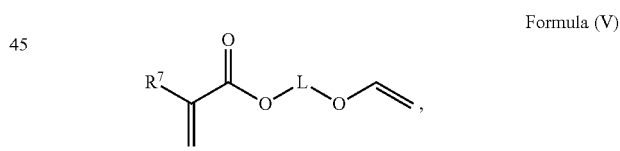

Formula (V)

wherein, R$^7$ represents a hydrogen or a methyl group; and L represents a divalent linking group selected from the group consisting of a substituted or unsubstituted alkylene group, a substituted or unsubstituted alkenylene group, a substituted or unsubstituted alkynylene group, a substituted or unsubstituted cycloalkylene group and an ether containing alkylene group.

In the most preferred embodiment R$^7$ represents hydrogen.

In one embodiment, radiation curable compositions comprising at least 50% by weight of the monomers according to Formula (V) of the total monomer composition are preferred, 60% by weight being more preferred and 70% by weight being the most preferred.

In a further preferred embodiment, the monomer according to Formula (IV) or (V) has a structure according to Formula (VI):

Formula (VI)

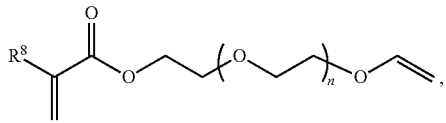

wherein, $R^8$ represents a hydrogen or a methyl group; and n represents an integer from 0 to 4. In the most preferred embodiment $R^8$ represents hydrogen and n is equal to 1.

Preferred examples of monomers include

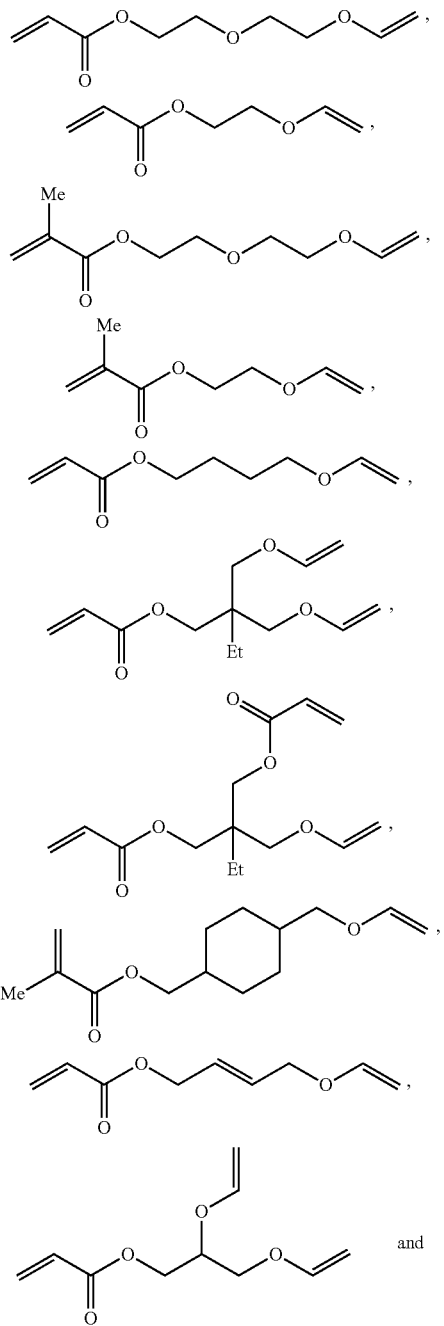

and

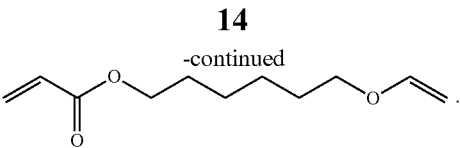

A single polymerizable thioxanthone according to a preferred embodiment of the present invention can be used in the radiation curable composition. However, the use of a mixture of one or more polymerizable thioxanthones, and optionally other photoinitiators, preferably polymerizable photoinitiators, is advantageous. The advantage is that the absorption spectrum of UV radiation is enlarged and/or synergistic effects between photoinitiators are obtained, thereby speeding up the polymerization of the monomers and oligomers in the radiation curable composition. Thioxanthones are known to be used as a "sensitizer" in some radiation curable compositions and the polymerizable thioxanthones can equally be used as sensitizer in such radiation curable compositions.

A preferred amount of the polymerizable thioxanthone is 0-50 wt %, more preferably 0.1-20 wt %, and most preferably 0.3-15 wt % of the total weight of the radiation curable composition.

The radiation curable composition can be a colourless liquid, but preferably includes at least one colorant. In the case of radiation curable inkjet inks, such a colourless inkjet ink can, for example, be used to enhance the glossiness of an inkjet printed image.

The radiation curable compositions are preferably non-aqueous compositions. The term "non-aqueous" refers to a liquid carrier which should contain no water. However sometimes a small amount, generally less than 5 wt % of water based on the total weight of the composition or ink, can be present. This water was not intentionally added but came into the composition via other components as a contamination, such as for example polar organic solvents. Higher amounts of water than 5 wt % tend to make the radiation curable compositions and inks instable, preferably the water content is less than 1 wt % based on the total weight of radiation curable composition or ink and most preferably no water at all is present.

The radiation curable compositions and inks preferably do not contain an evaporable component such as an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC, and preferably 0.1-10.0 wt %, and particularly preferably 0.1-5.0 wt %, each based on the total weight of the curable composition.

The radiation curable composition is preferably a radiation curable inkjet ink including no organic solvent or water.

A free radical radiation curable inkjet ink set includes at least two different inkjet inks, wherein at least one inkjet ink preferably contains one or more colorants, preferably one or more colour pigments.

The curable ink set preferably comprises at least one yellow curable ink (Y), at least one cyan curable ink (C) and at least one magenta curable ink (M) and preferably also at least one black curable ink (K). The curable CMYK-ink set may also be extended with extra inks such as red, green, blue, and/or orange to further enlarge the colour gamut of the image. The CMYK-ink set may also be extended by the combination of the full density inkjet inks with light density inkjet inks. The combination of dark and light colour inks and/or black and grey inks improves the image quality by a lowered graininess.

The pigmented radiation curable ink preferably contains a dispersant, more preferably a polymeric dispersant, for dispersing the pigment. The pigmented curable ink may contain a dispersion synergist to improve the dispersion quality and stability of the ink. Preferably, at least the magenta ink contains a dispersion synergist. A mixture of dispersion synergists may be used to further improve dispersion stability.

The viscosity of the radiation curable composition or inkjet ink is preferably smaller than 20 mPa·s at 45° C. and at a shear rate of 1,000 s$^{-1}$, more preferably between 1 and 14 mPa·s at 45° C. and a shear rate of 1,000 s$^{-1}$.

For high speed, high resolution printing, the viscosity measured at 45° C. is preferably smaller than 10 mPa·s at 45° C. and at a shear rate of 90 s$^{-1}$. Such measurement can be performed using a Brookfield DV-II+ viscometer at 45° C. and at 12 rotations per minute.

The radiation curable composition or inkjet ink may further also contain at least one surfactant for obtaining good spreading characteristics on a substrate.

The static surface tension of the radiation curable composition or inkjet ink is preferably in the range of about 20 mN/m to about 70 mN/m at 25° C., more preferably in the range of about 22 mN/m to about 40 mN/m at 25° C. The static surface tension is preferably measured with a KRÜSS tensiometer K9 from KRÜSS GmbH, Germany at 25° C. after 60 seconds.

The radiation curable composition preferably has a dynamic surface tension of no more than 30 mN/m measured by maximum bubble pressure tensiometry at a surface age of 50 ms and at 25° C. The dynamic surface tension is measured using a Bubble Pressure Tensiometer BP2 available from KRÜSS.

The radiation curable composition or inkjet ink may further also contain at least one inhibitor for improving the thermal stability of the ink.

Other Photoinitiators and Co-Initiators

The polymerizable thioxanthone according to a first aspect of the present invention may be combined with one or more other initiators and/or synergists, preferably amine synergists. Both type I and type II photoinitiators can be used in the present invention, alone or in combination. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or co-initiator.

In a preferred embodiment, the radiation curable composition includes a combination of the polymerizable thioxanthone and one or more acylphosphine oxide type of initiators, optionally further combined with one or more amine synergists. Such a combination has been found to be advantageous in curing speed, especially in a photoinitiating system for LED curable compositions.

In a further preferred embodiment, the polymerizable thioxanthone according to the present invention is used in combination with one or more acylphosphine oxide photoinitiators selected from the group consisting of bis(2,4,6-trimethylbenzoyl)-phenylphosphine oxide; 2,4,6-trimethylbenzoyl-diphenyl-phosphineoxide; and 2,4,6-trimethylbenzoyl-phenyl-phosphinic acid ethyl ester.

Suitable commercially available acylphosphine oxide photoinitiators include Irgacure™ 819, Lucirin™ TPO-L available from BASF, Omnirad™ TPO and Omnirad™ TPO-L from IGM Resins.

In a preferred embodiment, the polymerizable thioxanthones according to the present invention are preferably used in combination with at least one oligomeric, multifunctional or polymerizable ethylenically unsaturated co-initiator, preferably selected from the group consisting of aliphatic tertiary amines and dialkylamino substituted aromatic compounds, dialkylamino substituted aromatic compounds being more preferred, 4-dialkylamino benzoic acid derivatives being the most preferred.

Other suitable photo-initiators are disclosed in CRIVELLO, J. V., et al. VOLUME III: Photoinitiators for Free Radical Cationic. 2nd edition. Edited by BRADLEY, G. London, UK: John Wiley and Sons Ltd, 1998. p.287-294. Preferably diffusion hindered analogues of these photoinitiators are used.

A diffusion hindered photoinitiator is a photoinitiator which exhibits a much lower mobility in a cured layer of the curable composition or ink than a monofunctional photoinitiator, such as benzophenone. Several methods can be used to lower the mobility of the photoinitiator. One way is to increase the molecular weight of the photoinitiator so that the diffusion speed is reduced, e.g. polymeric photoinitiators. Another way is to increase its reactivity so that it is built into the polymerizing network, e.g. multifunctional photoinitiators (having 2, 3 or more photoinitiating groups) and polymerizable photoinitiators. The diffusion hindered photoinitiator is preferably selected from the group consisting of non-polymeric multifunctional photoinitiators and polymerizable photoinitiators. Non-polymeric di- or multifunctional photoinitiators usually have a molecular weight between 300 and 900 Dalton. Non-polymerizable monofunctional photoinitiators with a molecular weight in that range are not diffusion hindered photoinitiators. Most preferably the diffusion hindered photoinitiator is a polymerizable initiator since the effect on viscosity increase of the radiation curable composition is much smaller compared to other type of diffusion hindered initiators such as polymeric photoinitiators.

A suitable diffusion hindered photoinitiator may contain one or more photoinitiating functional groups derived from a Norrish type I-photoinitiator selected from the group consisting of benzoinethers, benzil ketals, α,α-dialkoxyacetophenones, α-hydroxyalkylphenones, α-aminoalkylphenones, acylphosphine oxides, acylphosphine sulfides, α-haloketones, α-halosulfones and phenylglyoxalates.

A suitable diffusion hindered photoinitiator may contain one or more photoinitiating functional groups derived from a Norrish type II-initiator selected from the group consisting of benzophenones, thioxanthones, 1,2-diketones and anthraquinones.

Suitable diffusion hindered photoinitiators are also those disclosed in EP 2053101 A (AGFA) in paragraphs [0074] and for difunctional and multifunctional photoinitiators, in paragraphs [0077] to [0080] for polymeric photoinitiators and in paragraphs [0081] to [0083] for polymerizable photoinitiators.

Other preferred polymerizable photoinitiators are those disclosed in EP 2065362 A (AGFA) and EP 2161264 A (AGFA).

Preferred diffusion hindered co-initiators are disclosed in paragraphs [0064] to [0069] of EP 2444429 A (AGFA).

A preferred amount of the other photoinitiators and/or co-initiators is 0-50 wt %, more preferably 0.1-20 wt %, and most preferably 0.3-15 wt % of the total weight of the radiation curable composition or inkjet ink.

Monomers and Oligomers

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri-and higher functionality monomers, oligomers and/or prepolymers may be used. The viscosity of the radiation curable compositions and inks can be adjusted by varying the ratio between the monomers and oligomers.

Particularly preferred monomers and oligomers are those listed in [0106] to [0115] in EP 1911814 A (AGFA).

For achieving high printing speeds, low viscous monomers are used so that a low viscosity for the radiation curable inkjet ink can be obtained. A popular low viscosity monomer is tetrahydrofurfuryl(meth)acrylate. However, in industrial inkjet printing also a high reliability is required which allows the incorporation of the inkjet printing system into a production line.

It was found that a vessel of tetrahydrofurfuryl acrylate kept at 40° C. for 100 hours lost 40% of its weight. Printing heads in the present method preferably operate at temperatures between 35 to 45° C. A high evaporation of tetrahydrofurfuryl(meth)acrylate from a print head nozzle during a stand-by mode from the inkjet printer leads to an unacceptable increase in viscosity of the inkjet ink in the print head and subsequently to jetting failures of the print head (bad latency). The radiation curable inkjet inks preferably use low viscosity monomers exhibiting small evaporation rates such as vinylether (meth)acrylates. For example, 2-(2-vinyloxyethoxy)ethyl acrylate (VEEA) kept at 40° C. for 100 hours loses only 8% of its weight.

Another advantage of VEEA and other vinylether(meth)acrylates is that it is a bifunctional monomer having two different polymerizable groups, namely an acrylate group and an ether group. This allows a better control of the polymerization rate, whereby the amount of extractable and migrateable monomer is reduced. This reduces health risks to inkjet printer operators or allows for printing e.g. food packaging materials that are subject to strict safety regulations.

In a preferred embodiment, the radiation curable inkjet ink includes a monomer including at least one acrylate group and at least one ethylenically unsaturated polymerizable group selected from the group consisting of allylether, allylester, allylcarbonate, vinyl ether, vinylester, vinylcarbonate, fumarate, and maleate. Preferred examples of such monomers are disclosed in EP 2053101 A (AGFA).

In a preferred embodiment, the polymerizable composition of the radiation curable inkjet ink consists essentially of: a) 25-100 wt % of one or more polymerizable compounds A having at least one acrylate group and at least one second ethylenically unsaturated polymerizable functional group selected from the group consisting of a vinyl ether group, an allylether group and a allylester group; b) 0-55 wt % of one or more polymerizable compounds B selected from the group consisting of monofunctional acrylates and difunctional acrylates; and c) 0-55 wt % of one or more polymerizable compounds C selected from the group consisting of trifunctional acrylates, tetrafunctional acrylates, pentafunctional acrylates and hexafunctional acrylates, with the proviso that if the weight percentage of compounds B>24 wt %, then the weight percentage of compounds C>1 wt %; and wherein all weight percentages of A, B and C are based upon the total weight of the polymerizable composition; and with the proviso that at least one polymerizable compound B or C is present in the polymerizable composition if the free radical curable inkjet ink contains no initiator. Such a composition allows for safe inkjet printing on food packaging materials.

The monomers and oligomers used in radiation curable compositions and inkjet inks are preferably purified compounds having no or almost no impurities, more particularly no carcinogenic, mutagenic or reprotoxic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

The radiation curable composition and inkjet ink preferably includes 60 to 95 wt % of polymerizable compounds, more preferably 70 to 90 wt % of polymerizable compounds based upon the total weight of the radiation curable inkjet ink or varnish. A colourless inkjet ink may include up to 99 wt % of polymerizable compounds based upon the total weight of the radiation curable inkjet ink.

Inhibitors

The radiation curable compositions and inkjet inks may contain a polymerization inhibitor. Preferred polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol (=BHT) may also be used.

Preferred commercial inhibitors are, for example, Sumilizer™ GA-80, Sumilizer™ GM and Sumilizer™ GS produced by Sumitomo Chemical Co. Ltd.; Genorad™ 16, Genorad™ 18 and Genorad™ 20 from Rahn AG; Irgastab™ UV10 and Irgastab™ UV22, Tinuvin™ 460 and CGS20 from Ciba Specialty Chemicals; Floorstab™ UV range (UV-1, UV-2, UV-5 and UV-8) from Kromachem Ltd, Additol™ S range (S100, 5110, 5120 and 5130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably less than 5 wt %, more preferably less than 3 wt %, and most preferably less than 2 wt % of the total radiation curable composition or ink.

Colorants

Colorants used in the radiation curable compositions may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. A colour pigment may be chosen from those disclosed by HERBST, Willy, et al. Industrial Organic Pigments, Production, Properties, Applications. 3rd edition. Wiley-VCH, 2004. ISBN 3527305769.

Preferred pigments are disclosed in paragraphs [0128] to [0138] of WO 2008/074548 (AGFA).

Also mixed crystals may be used. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia™ Magenta RT-355-D from Ciba Specialty Chemicals.

Also mixtures of pigments may be used in the pigment dispersions. For some inkjet applications, a neutral black inkjet ink is preferred and can be obtained, for example, by mixing a black pigment and a cyan pigment into the ink. The inkjet application may also require one or more spot colours, for example for packaging inkjet printing or textile inkjet printing. Silver and gold are often desired colours for inkjet poster printing and point-of-sales displays.

Non-organic pigments may be used in the pigment dispersions. Particular preferred pigments are C.I. Pigment Metal 1, 2 and 3. Illustrative examples of the inorganic pigments include red iron oxide (III), cadmium red, ultramarine blue, prussian blue, chromium oxide green, cobalt green, amber, titanium black and synthetic iron black.

Pigment particles in inkjet inks should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. An average particle size smaller than 0.050 μm is less desirable for decreased light-fastness, but mainly also because very small pigment particles or individual pigment molecules thereof may still be extracted in food packaging applications. The average particle size of pigment particles is determined with a Brookhaven Instruments Particle Sizer BI90plus based upon the principle of dynamic light scattering. The ink is diluted with ethyl acetate to a pigment concentration of 0.002 wt %. The measurement settings of the BI90plus are: 5 runs at 23° C., angle of 90°, wavelength of 635 nm and graphics=correction function However for white pigment dispersions, the numeric average particle diameter of the white pigment is preferably from 200 to 500 nm, more preferably from 220 to 400 nm, and most preferably from 240 to 320 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a Malvern™ nano-S available from Goffin-Meyvis. A sample can, for example, be prepared by addition of one drop of ink to a cuvette containing 1.5 mL ethyl acetate and mixed until a homogenous sample was obtained. The measured particle size is the average value of 3 consecutive measurements consisting of 6 runs of 20 seconds.

Suitable white pigments are given by Table 2 in [0116] of WO 2008/074548 (AGFA). The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548 (AGFA).

The pigments are preferably present in the range of 0.01 to 15%, more preferably in the range of 0.05 to 10% by weight and most preferably in the range of 0.1 to 5% by weight, each based on the total weight of the pigment dispersion. For white pigment dispersions, the white pigment is preferably present in an amount of 3% to 30% by weight of the pigment dispersion, and more preferably 5% to 25%. An amount of less than 3% by weight cannot achieve sufficient covering power and usually exhibits very poor storage stability and ejection property.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);
alternating polymerized monomers (e.g. monomers A and B polymerized into ABABABAB);
gradient (tapered) polymerized monomers (e.g. monomers A and B polymerized into AAABAABBABBB);
block copolymers (e.g. monomers A and B polymerized into AAAAABBBBBB) wherein the block length of each of the blocks (2, 3, 4, 5 or even more) is important for the dispersion capability of the polymeric dispersant;
graft copolymers (graft copolymers consist of a polymeric backbone with polymeric side chains attached to the backbone); and
mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100000, more preferably smaller than 50000 and most preferably smaller than 30000.

The polymeric dispersant has preferably a polydispersity PD smaller than 2, more preferably smaller than 1.75 and most preferably smaller than 1.5.

Commercial examples of polymeric dispersants are the following:

DISPERBYK™ dispersants available from BYK CHEMIE GMBH;
SOLSPERSE™ dispersants available from NOVEON;
TEGO™ DISPERS™ dispersants from EVONIK;
EDAPLAN™ dispersants from MÜNZING CHEMIE;
ETHACRYL™ dispersants from LYONDELL;
GANEX™ dispersants from ISP;
DISPEX™ and EFKA™ dispersants from CIBA SPECIALTY CHEMICALS INC (BASF);
DISPONER™ dispersants from DEUCHEM; and
JONCRYL™ dispersants from JOHNSON POLYMER.

Particularly preferred polymeric dispersants include Solsperse™ dispersants from NOVEON, Efka™ dispersants from CIBA SPECIALTY CHEMICALS INC (BASF) and Disperbyk™ dispersants from BYK CHEMIE GMBH. Particularly preferred dispersants are Solsperse™ 32000, 35000 and 39000 dispersants from NOVEON.

The polymeric dispersant is preferably used in an amount of 2 to 600 wt %, more preferably 5 to 200 wt % and most preferably 50 to 100 wt % based on the weight of the pigment.

Dispersion Synergists

A dispersion synergist usually consists of an anionic part and a cationic part. The anionic part of the dispersion synergist usually exhibits a certain molecular similarity with the colour pigment and the cationic part of the dispersion synergist consists of one or more protons and/or cations to compensate the charge of the anionic part of the dispersion synergist.

The synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include Solsperse™ 5000 and Solsperse™ 22000 from NOVEON.

Particular preferred pigments for the magenta ink used are a diketopyrrolo-pyrrole pigment or a quinacridone pigment. Suitable dispersion synergists include those disclosed in EP 1790698 A (AGFA), EP 1790696 A (AGFA), WO 2007/060255 (AGFA) and EP 1790695 A (AGFA).

In dispersing C.I. Pigment Blue 15:3, the use of a sulfonated Cu-phthalocyanine dispersion synergist, e.g. Solsperse™ 5000 from NOVEON is preferred. Suitable dispersion synergists for yellow inkjet inks include those disclosed in EP 1790697 A (AGFA).

In a preferred embodiment, the dispersion synergist includes one, two or more carboxylic acid groups and preferably no sulfonic acid groups.

Surfactants

The radiation curable compositions and inks may contain a surfactant. The surfactant(s) can be anionic, cationic, non-ionic, or zwitter-ionic and are usually added in a total quantity less than 10 wt % based on the total weight of the radiation curable composition or ink and particularly in a total less than 5 wt % based on the total weight of the radiation curable composition or ink.

Surfactants reduce the surface tension of the ink in order to reduce the contact angle on the ink-receiver, i.e. to improve the wetting of the ink-receiver by the ink. On the other hand, the jettable ink must meet stringent performance criteria in order to be adequately jettable with high precision, reliability and during an extended period of time. To achieve both wetting of the ink-receiver by the ink and high jetting performance, typically, the surface tension of the ink is reduced by the addition of one or more surfactants. In the case of curable inkjet inks, however, the surface tension of the inkjet ink is not only determined by the amount and type of surfactant, but also by the polymerizable compounds, the polymeric dispersants and other additives in the ink composition.

Suitable surfactants include fluorinated surfactants, fatty acid salts, ester salts of a higher alcohol, alkylbenzene sulphonate salts, sulphosuccinate ester salts and phosphate ester salts of a higher alcohol (for example, sodium dodecylbenzenesulphonate and sodium dioctylsulphosuccinate), ethylene oxide adducts of a higher alcohol, ethylene oxide adducts of an alkylphenol, ethylene oxide adducts of a polyhydric alcohol fatty acid ester, and acetylene glycol and ethylene oxide adducts thereof (for example, polyoxyethylene nonylphenyl ether, and SURFYNOL™ 104, 104H, 440, 465 and TG available from AIR PRODUCTS & CHEMICALS INC.).

Preferred surfactants include fluoro surfactants (such as fluorinated hydrocarbons) and silicone surfactants. The silicones are typically siloxanes and can be alkoxylated, polyether modified, polyester modified, polyether modified hydroxy functional, amine modified, epoxy modified and other modifications or combinations thereof. Preferred siloxanes are polymeric, for example polydimethylsiloxanes.

Examples of useful commercial silicone surfactants are those supplied by BYK CHEMIE GMBH (including Byk™-302, 307, 310, 331, 333, 341, 345, 346, 347, 348, UV3500, UV3510 and UV3530), those supplied by TEGO CHEMIE SERVICE (including Tego Rad™ 2100, 2200N, 2250, 2300, 2500, 2600 and 2700), Ebecryl™ 1360 a polysilixone hexaacrylate from CYTEC INDUSTRIES BV and Efka™-3000 series (including Efka™-3232 and Efka™-3883) from EFKA CHEMICALS B.V.

The fluorinated or silicone compound used as a surfactant is preferably a cross-linkable surfactant. Suitable polymerizable compounds having surface-active effects include, for example, polyacrylate copolymers, silicone modified acrylates, silicone modified methacrylates, acrylated siloxanes, polyether modified acrylic modified siloxanes, fluorinated acrylates, and fluorinated methacrylate. These acrylates can be mono-, di-, tri- or higher functional (meth)acrylates.

Depending upon the application a surfactant can be used with a high, low or intermediate dynamic surface tension. Silicone surfactants are generally known to have low dynamic surface tensions while fluorinated surfactants are known to have higher dynamic surface tensions.

Silicone surfactants are often preferred in curable inkjet compositions and inks, especially the reactive silicone surfactants, which are able to be polymerized together with the polymerizable compounds during the curing step.

Preparation of Pigmented Radiation Curable Compositions and Inks

The average particle size and distribution of a pigment is an important feature for inkjet inks. The inkjet ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can comprise particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and as much as possible under light conditions in which actinic radiation has been substantially excluded.

The inkjet ink may contain more than one pigment, and may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture comprise the mill grind and the milling media. The mill grind comprises pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, mechanical devices and residence conditions selected, the initial and desired final particle size, etc. In a preferred embodiment of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make inkjet inks in the form of a concentrated mill grind, which is subsequently diluted to the appropriate concentration for use in the inkjet printing system. This technique permits preparation of a greater quantity of pigmented ink from the equipment. By dilution, the inkjet ink is adjusted to the desired viscosity, surface tension, colour, hue, saturation density, and print area coverage for the particular application.

Inkjet Printing Methods

Another aspect of the present invention is a method of inkjet printing including the step of applying or jetting a radiation curable composition including the polymerizable thioxanthone as defined above onto a substrate. The radiation curable composition can be applied to the substrate by coating or printing, e.g. flexographic printing.

The polymerizable thioxanthone preferably used for initiating the polymerization of monomers in a radiation curable composition by using UV radiation with a wavelength larger than 360 nm, more preferably larger than 380 nm.

The inkjet printing method preferably includes the steps of:

a) providing a radiation curable composition including a polymerisable thioxanthone according to a preferred embodiment of the present invention to an inkjet printing device;

b) depositing the radiation curable composition with the inkjet printing device on a substrate; and c) at least partially curing the radiation curable composition by using UV radiation with a wavelength larger than 360 nm.

Substrates

Another aspect of the present invention is a substrate having a cured layer of the radiation curable composition including the polymerizable thioxanthone as defined above.

In a preferred embodiment, the substrate is a substantially non-absorbing ink-receiver. The term "substantially non-absorbing ink-jet ink-receiver" means any ink-jet ink-receiver which fulfills at least one of the following two criteria:

1) No penetration of ink into the ink-jet ink-receiver deeper than 2 μm;

2) No more than 20% of a droplet of 100pL jetted onto the surface of the ink-jet ink-receiver disappears into the ink-jet ink-receiver in 5 seconds. If one or more coated layers are present, the dry thickness should be less than 5 μm. Standard analytical method can be used by one skilled in the art to determine whether an ink-receiver falls under either or both of the above criteria of a substantially non-absorbing ink-receiver. For example, after jetting ink on the ink-receiver surface, a slice of the ink-receiver can be taken and examined by transmission electron microscopy to determine if the penetration depth of the ink is greater than 2μm. Further information regarding suitable analytical methods can be found in the article: DESIE, G, et al. Influence of Substrate Properties in Drop on Demand Printing. *Proceedings of Imaging Science and Technology's* 18*th International Conference on Non Impact Printing.* 2002, p.360-365.

Inkjet Printing Devices

The radiation curable inkjet compositions and inks may be jetted by one or more print heads ejecting small droplets of ink in a controlled manner through nozzles onto an ink-receiver surface, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to the present invention is not restricted to piezoelectric inkjet printing. Other inkjet print heads can be used and include various types, such as a continuous type and thermal, electrostatic and acoustic drop on demand type.

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

Curing Devices

The radiation curable compositions and inkjet inks may be cured by exposing them to actinic radiation, preferably by ultraviolet radiation.

In inkjet printing, the curing devices may be arranged in combination with the print head of the inkjet printer, travelling therewith so that the curable composition is exposed to curing radiation very shortly after been jetted.

In such an arrangement it can be difficult to provide a small enough radiation source connected to and travelling with the print head, such as a light emitting diode (LED). Therefore, a static fixed radiation source may be employed, e.g. a source of curing UV-light, connected to the radiation source by a flexible radiation conductor such as a fiber optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:

UV-A: 400 nm to 320 nm

UV-B: 320 nm to 290 nm

UV-C: 290 nm to 100 nm.

In a preferred embodiment of the method of inkjet printing according to the present invention, the inkjet printing device contains one or more UV LEDs with a wavelength larger than 360 nm, preferably one or more UV LEDs with a wavelength larger than 380 nm, and most preferably UV LEDs with a wavelength of about 395 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

INDUSTRIAL APPLICABILITY

The polymerizable thioxanthone can be used to prepare radiation curable compositions, flexographic inks and inkjet inks which after curing are required to have minimal extractable and volatile compounds, such as food packaging applications involving, for example, short run packaging inkjet printing or flexographic printing on packaging materials.

However, the polymerisable photoinitiator may also be used in radiation curable compositions and inks which have less strict regulations on extractables and volatiles, such as e.g. billboard or poster printing, since it enhances the safety for the operator in preparing these billboards and posters.

The polymerisable photoinitiator can also be advantageously used not only in the preparation of lithographic printing plates as exemplified by US 2008008966 (FUJIFILM) or flexographic printing plates as exemplified by US 2006055761 A (AGFA), but also in the preparation of flexographic or lithographic radiation curing inks to be used with these printing plates as exemplified in US 2009018230 (CIBA).

EXAMPLES

Materials

All materials used in the following examples were readily available from standard sources such as ALDRICH CHEMICAL Co. (Belgium) and ACROS (Belgium) unless otherwise specified.

Lewatit™ M600 MB is available from CLEARTECH INDUSTRIES INC. Activated Lewatit™ M600 MB means that it received an alkaline treatment according to the following method: 25 g of Lewatit™ M600 MB was treated with 75 mL of 1 N sodium hydroxide solution and stirred for 2 hours. The ion exchanger was isolated by filtration, washed several times with water and dried until constant weight.

DB 162 is the isolated polymer from Disperbyk™ 162, supplied as a 40% solution in a mixture of 2-methoxy-1-methyl-acetate, xylene and butylacetate by BYK Chemie. The polymer has been isolated by precipitation with iso-octane, followed by washing and drying.

EFKA™ 7701 is a butylacrylate-vinylpyridine copolymer having an amine value of 40 mg KOH/g available from BASF.

Sun Fast™ Blue 15:4 is a C.I. Pigment Blue 15:4 pigment from SUN CHEMICAL.

Symuler™ Brilliant Carmine 6B350SD is a C.I. Pigment Red 57:1 from SUN CHEMICAL.

Cromophtal™ Yellow LA2 is a C.I. Pigment Yellow 150 from BASF (CIBA SPECIALTY CHEMICALS).

Mogul™ E is a carbon black pigment from CABOT CORP.

VEEA is 2-(2'-vinyloxyethoxy)ethylacrylate, a difunctional monomer available from NIPPON SHOKUBAI, Japan.

Genorad™ 16 is a stabilizer supplied by RAHN.

C-DISP

A 30 wt % solution of DB162 in 2-(2-vinyloxyethoxy)ethylacrylate was prepared. 1 wt % Genorad™ 16 was added. 1.5 kg Sun Fast™ Blue 15:4 was added to a mixture of 1.95 kg 2-(2'-vinyloxyethoxy)ethylacrylate, 2.5 kg of the DB162 solution and 50 g Genorad™ 16, while stirring with a DISPERLUX™ dispenser. Stirring was continued for 30 minutes. The vessel was connected to a DYNO™-MILL ECM Poly mill from the company Willy A. Bachofen (Switzerland), preloaded with 1.5 kg 2-(2'-vinyloxyethoxy)ethyl acrylate and filled for 42% with 0.4 mm yttrium stabilized zirconia beads ("high wear resistant zirconia grinding media" from TOSOH Co.). The mixture was circulated over the mill for 5 hours 52 minutes at a flow rate of 1.5 l/min and a rotation speed in the mill of about 13 m/s. During the milling procedure, an additional 2.5 kg of the DB162 solution was added. During the complete milling procedure the content in the mill was cooled to keep the temperature below 40° C. After milling, dispersion 1 was discharged into a 15 L-vessel. The resulting concentrated pigment dispersion C-DISP according to Table 2 exhibited an average particle size of 85 nm.

TABLE 2

| Component | wt % |
| --- | --- |
| Sun Fast ™ Blue 15:4 | 15.0 |
| DB162 | 15.0 |
| Genorad ™ 16 | 1.0 |
| VEEA | 69.0 |

M-DISP is a magenta dispersion prepared as follows. 0.1 kg Irgastab™ UV10, 20.85 kg VEEA and 3.75 kg EFKA™ 7701 were mixed in a 60 l vessel. The vessel was connected to a DYNO™-MILL ECM Poly mill from the company Willy A. Bachofen (Switzerland), preloaded with 5.3 kg VEEA and filled for 42% with 0.4 mm yttrium stabilized zirconia beads ("high wear resistant zirconia grinding media" from TOSOH Co.) and the mixture was circulated for 5 minutes over the mill and discharged in the 60 l vessel. 7.5 kg of Symuler™ Brilliant Carmine 6B350SD was added, while stirring with a DISPERLUX™ disperser (from DISPERLUX S.A.R.L., Luxembourg). Stirring was continued for 30 minutes. The vessel was connected again to the mill and the mixture was circulated over the mill for 4 hours and 10 minutes at a flow rate of 8 l/min and a rotation speed in the mill of 14.7 m/s. During the milling procedure, an additional 3.75 kg EFKA™ 7701 was added, followed by the addition of 8.75 kg VEEA. During the complete milling procedure the content in the mill was cooled to keep the temperature below 40° C. After milling, the dispersion was discharged into a 60 L-vessel. The resulting concentrated pigment dispersion M-DISP according to Table 3 exhibited an average particle size of 131 nm.

TABLE 3

| Component | wt % |
| --- | --- |
| Symuler ™ Brilliant Carmine 6B350SD | 15.0 |
| EFKA ™ 7701 | 15.0 |
| Irgastab ™ UV 10 | 0.2 |
| VEEA | 69.8 |

Y-DISP is a yellow dispersion prepared as follows. A 30 wt % solution of DB162 in VEEA was prepared. 1 wt % Genorad™ 16 was added. 1.5 kg Cromophtal™ Yellow LA2 was added to a mixture of 1.95 kg VEEA, 2.5 kg of the DB162 solution and 50 g Genorad™ 16, while stirring with a DISPERLUX™ disperser (from DISPERLUX S.A.R.L., Luxembourg). Stirring was continued for 30 minutes. The vessel was connected to a DYNO™-MILL ECM Pilot mill from the company Willy A. Bachofen (Switzerland), preloaded with 1.5 kg VEEA and filled for 42% with 0.4 mm yttrium stabilized zirconia beads ("high wear resistant zirconia grinding media" from TOSOH Co.). The mixture was circulated over the mill for 5 hours 52 minutes at a flow rate of 1.5 l/min and a rotation speed in the mill of about 13 m/s. During the milling procedure, an additional 2.5 kg of the DB162 solution was added. During the complete milling procedure the content in the mill was cooled to keep the temperature below 40° C. After milling, the dispersion was discharged into a 15 L-vessel. The resulting concentrated pigment dispersion Y-DISP according to Table 4 exhibited an average particle size of 148 nm.

TABLE 4

| Component | wt % |
| --- | --- |
| Cromophtal ™ Yellow LA2 | 15.0 |
| DB162 | 15.0 |
| Genorad ™ 16 | 1.0 |
| VEEA | 69.0 |

K-DISP is a black dispersion prepared as follows.

A 30 wt % solution of DB162 in VEEA was prepared. 0.05 kg Irgastab™ UV10, 5.900 kg VEEA and 12.5 kg of the 30 wt % solution of DB162 were mixed in a 60 l vessel. The vessel was connected to a DYNO™-MILL ECM Poly mill from the company Willy A. Bachofen (Switzerland), preloaded with 5.3 kg VEEA and filled for 42% with 0.4 mm yttrium stabilized zirconia beads ("high wear resistant zirconia grinding media" from TOSOH Co.) and the mixture was circulated for 5 minutes over the mill and discharged in the 60 l vessel. 7.5 kg of Mogul™ E was added, while stirring with a DISPERLUX™ disperser (from DISPERLUX S.A.R.L., Luxembourg). Stirring was continued for 30 minutes. The vessel was connected again to the mill and the mixture was circulated over the mill for 3 hours and 57 minutes at a flow rate of 1.5 k/min and a rotation speed in the mill of 14.7 m/s. During the milling procedure, an additional 12.5 kg of the 30 wt % solution of DB162 was added, followed by the addition of 6.25 kg VEEA. During the complete milling procedure the content in the mill was cooled to keep the temperature below 40° C. After milling, the dispersion was discharged into a 60 L-vessel. The resulting concentrated pigment dispersion K-DISP according to Table 5 exhibited an average particle size of 127 nm.

TABLE 5

| Component | wt % |
| --- | --- |
| Mogul ™ E | 15.0 |
| DB162 | 15.0 |
| Irgastab ™ UV10 | 0.1 |
| VEEA | 69.9 |

COMPTX-1: is a polymerisable thioxanthone, having the following structure:

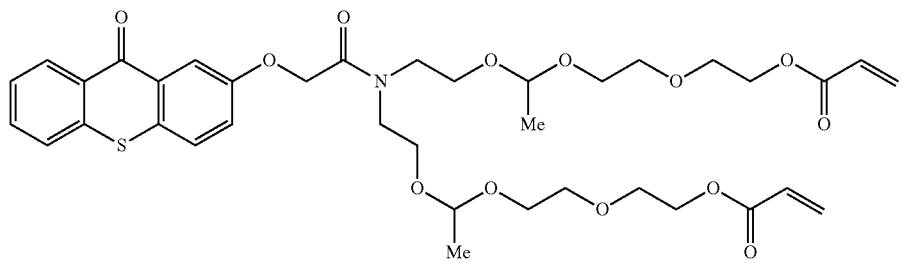 [SMILES: C=CC(=O)OCCOCCOC(C)OCCN(CCOC(C)OCCOCCOC(=O)C=C)C(=O)COc1ccc2sc3ccccc3c(=O)c2c1]

COMPTX-1 was prepared and used as a solution in VEEA as disclosed in Example 1 of EP 2199273 A (AGFA).

COMPTX-1SOL is a 43 wt % solution of COMPTX-1 in VEEA. The solution was prepared as follows. A mixture of 144.81 g (0.389 mol) of the amidothioxanthone (preparation as described in EP 2199273 A (AGFA)), 434 g VEEA and 1.71 g BHT was heated to 85° C. 11.11 g crosslinked poly (vinylpyridinium) tosylate was added and the reaction was allowed to continue for four and a half hours at 85° C. The reaction mixture was allowed to cool down to room temperature and the catalyst was removed by filtration. The solution was used as such in the comparative ink set. The concentration of COMPTX-1 was determined based on $^1$H-NMR analysis of the solution and found to be 43 wt %.

IC 819 is Irgacure™ 819, a bis-acyl-phosphineoxide photoinitiator supplied by BASF and having as chemical structure:

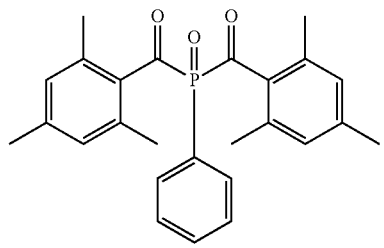

SC7040 is Speedcure™ 7040, a polymeric co-initiator supplied by LAMBSON.

Esacure™ KIP160 is a difunctional α-hydroxyketone available from LAMBERTI and having the chemical structure:

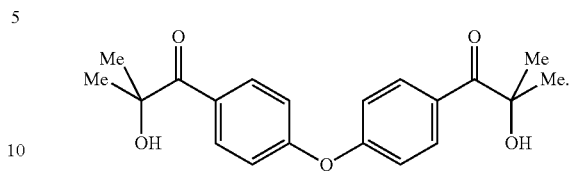

Type-I is a polymerisable Norrish type I initiator having the chemical structure:

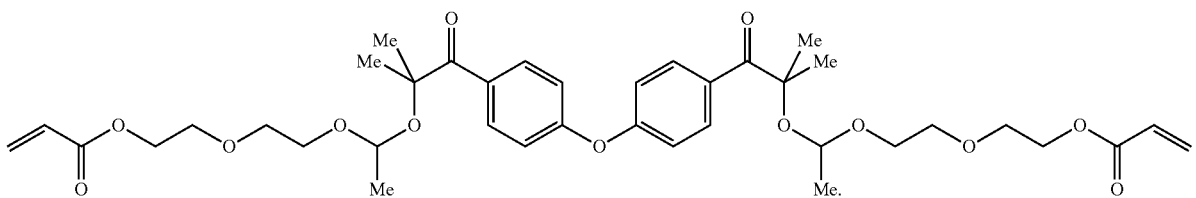 [SMILES: C=CC(=O)OCCOCCOC(C)OC(C)(C)C(=O)c1ccc(Oc2ccc(C(=O)C(C)(C)OC(C)OCCOCCOC(=O)C=C)cc2)cc1]

Type I was prepared as follows:

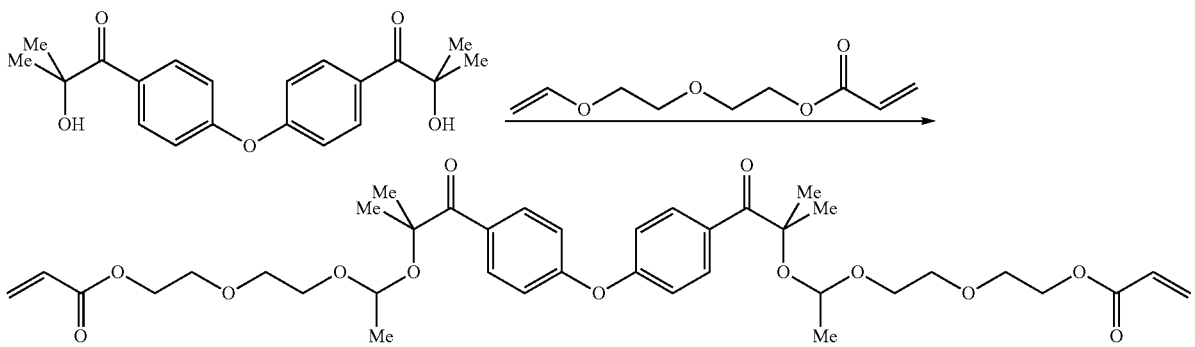

A mixture of 119.75 g (0.350 mol) Esacure™ KIP160, 380.10 g VEEA and 1.54 g BHT was heated to 85° C. 9.99 g of poly(vinylpryridinium)tosylate was added and the reaction was allowed to continue for 10 hours at 85° C. The reaction mixture was allowed to cool down to room temperature and the catalyst was removed by filtration. The solution was used as such in both the comparative and inventive ink set. The concentration was determined by $^1$H-NMR analysis of the solution. The initiator concentration was 51.6% by weight.

Omnipol™ 910 is a polymeric photoinitiator, supplied by IGM, having the following general structure:

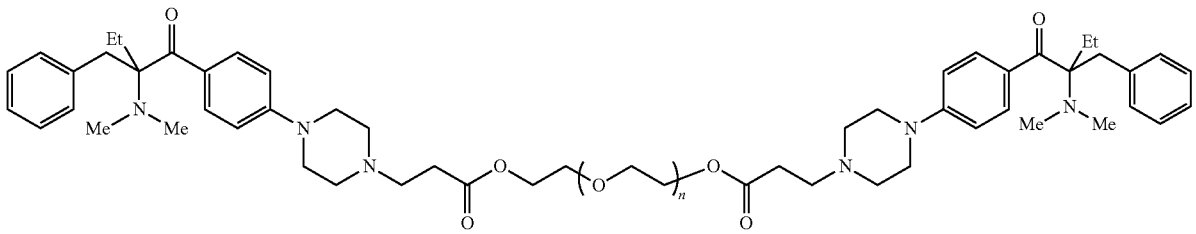

DPGDA is dipropyleneglycoldiacrylate from SARTOMER. Irgastab™ UV 10 is 4-hydroxy-2,2,6,6-tetramethylpiperidinooxy sebacate available from BASF.

Cupferron™ AL is aluminum N-nitrosophenylhydroxylamine from WAKO CHEMICALS LTD.

Stabi-1 is a mixture forming a polymerization inhibitor having a composition according to Table 6.

TABLE 6

| Component | wt % |
|---|---|
| DPGDA | 82.4 |
| p-methoxyphenol | 4.0 |
| 2,6-di-tert-butyl-4-methylphenol | 10.0 |
| Cupferron ™ AL | 3.6 |

UV3510 is Byk™ UV3510, a polyether modified polydimethylsiloxane, supplied by BYK Chemie GmbH.

PET100 is a 100 μm unsubbed biaxially stretched PET substrate with on the backside an antiblocking layer with antistatic properties available from AGFA-GEVAERT as P100C PLAIN/ABAS.

Measurement Methods

1. Curing Speed

A radiation curable composition was coated on a PET100 substrate using a bar coater and a 10 μm wired bar. The coated sample was fully cured using a Fusion DRSE-120 conveyor, equipped with a Fusion VPS/1600 lamp (D-bulb), which transported the sample under the UV-lamp on a conveyor belt at a speed of 50 m/min. The maximum output of the lamp was 1.05 J/cm$^2$ and a peak intensity of 5.6 W/cm$^2$. The percentage of the maximum output of the lamp was taken as a measure for curing speed, the lower the number the higher the curing speed. A sample was considered as fully cured at the moment scratching with a Q-tip caused no visual damage.

2. Average Particle Size

The particle size of pigment particles in a pigment dispersion was determined by photon correlation spectroscopy at a wavelength of 633 nm with a 4 mW HeNe laser on a diluted sample of the pigment dispersion. The particle size analyzer used was a Malvern™ nano-S available from Goffin-Meyvis.

The sample was prepared by addition of one drop of pigment dispersion to a cuvette containing 1.5 mL ethyl acetate and mixed until a homogenous sample was obtained. The measured particle size is the average value of 3 consecutive measurements consisting of 6 runs of 20 seconds.

3. Viscosity

The viscosity of a radiation curable composition was measured using a Haake Rotovisco RV1 at 40° C. and 1000s$^{-1}$.

Example 1

This example illustrates how the polymerizable thioxanthones according to preferred embodiments of the present invention can be prepared.

Example 1a

The Synthesis of Thioxanthone TX-1

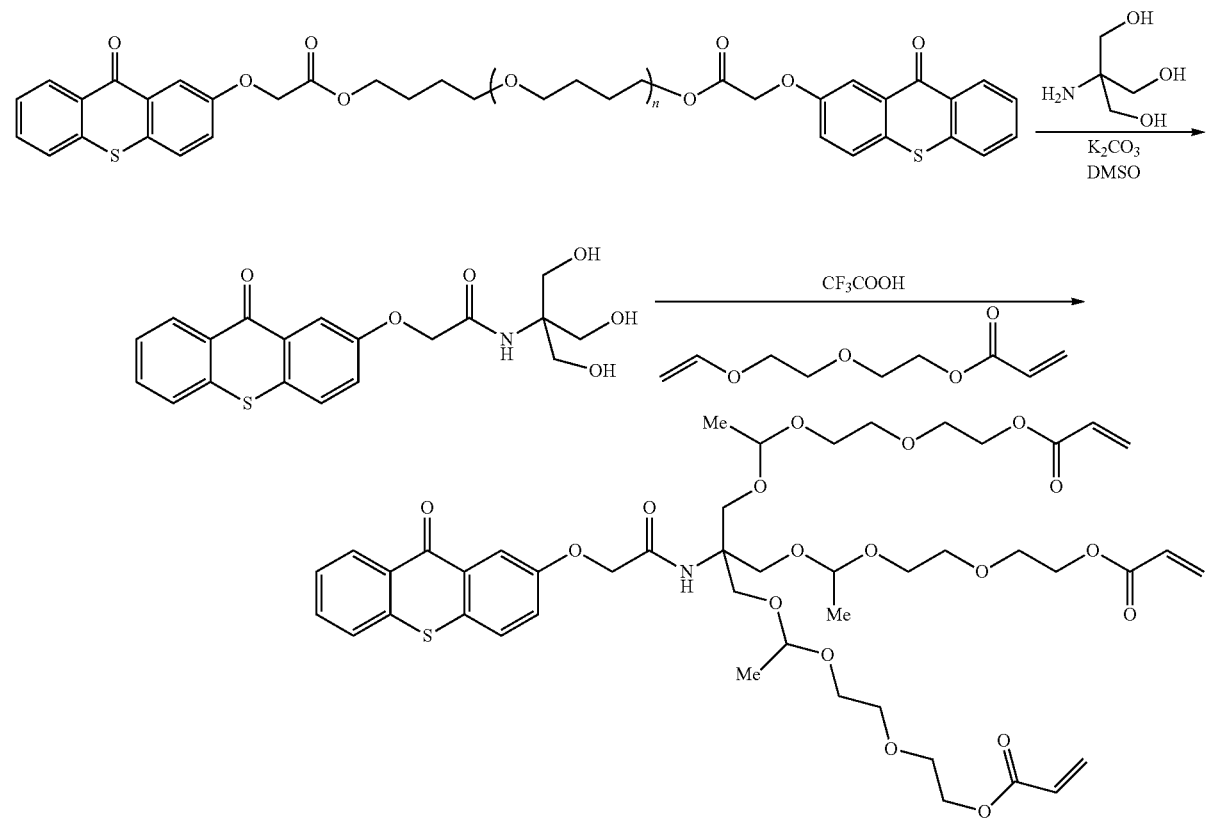

Step 1: The Aminolysis of Omnipol™ TX 395 g Omnipol™ TX, supplied by IGM, was dissolved in 1850 ml dimethyl sulfoxide. The reaction mixture was heated to 60° C. and 363 g (3 mol) tris(hydroxymethyl)aminomethane and 415 g (3 mol) potassium carbonate were added. The reaction was allowed to continue for 2 hours at 60° C. The reaction mixture was allowed to cool down to room temperature. The precipitated salts were removed by filtration and the reaction mixture was added to a mixture of 1500 ml water and 250 ml acetone. The intermediate thioxanthone precipitated from the medium, was isolated by filtration and dried. The crude thioxanthone was treated with 1500 ml acetone, isolated by filtration and dried. 260 g of the thioxanthone was isolated (TLC-analysis: RP-C18 (Partisil™ KC18F, supplied by Whatman), eluent MeOH/0.5 M NaCl, $R_f$=0.55). TLC analysis showed the presence of a small amount of an isomeric structure ($R_f$=0.60). The following structure was

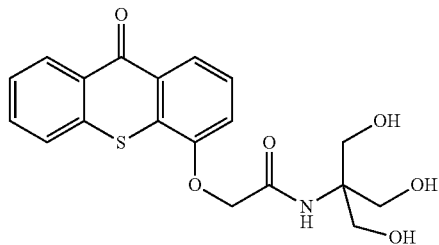 [SMILES: O=C(COc1cccc2c(=O)c3ccccc3sc12)NC(CO)(CO)CO]

assigned to the isomer:
The intermediate was further used as a mixture of the main isomer and the minor isomer.
Step 2: The Addition to VEEA:
22 g (58 mmol) of the amido-trihydroxy-thioxanthone was added to 227.8 g (1.224 mol) VEEA. 0.13 g (86 μl, 1.16 mmol) trifluoroacetic acid and 0.25 g (1.16 mmol) BHT were added and the mixture was heated to 77° C. The reaction was allowed to continue at 77° C. for 16 hours. The reaction was allowed to cool down to room temperature and 20 g of activated Lewatit M600 MB was added. The mixture was stirred for four hours at room temperature. The ion exchanger was removed by filtration. TX-1 was used as a solution in VEEA. (TLC-analysis: RP-C18 (Partisil™ KC18F, supplied by Whatman), eluent: MeOH/0.5 M NaCl 80/20, $R_f$=0.18). Based on TH-NMR analysis, the solution contained 19 wt % TX-1.

Example 1b

The Synthesis of Thioxanthone TX-2

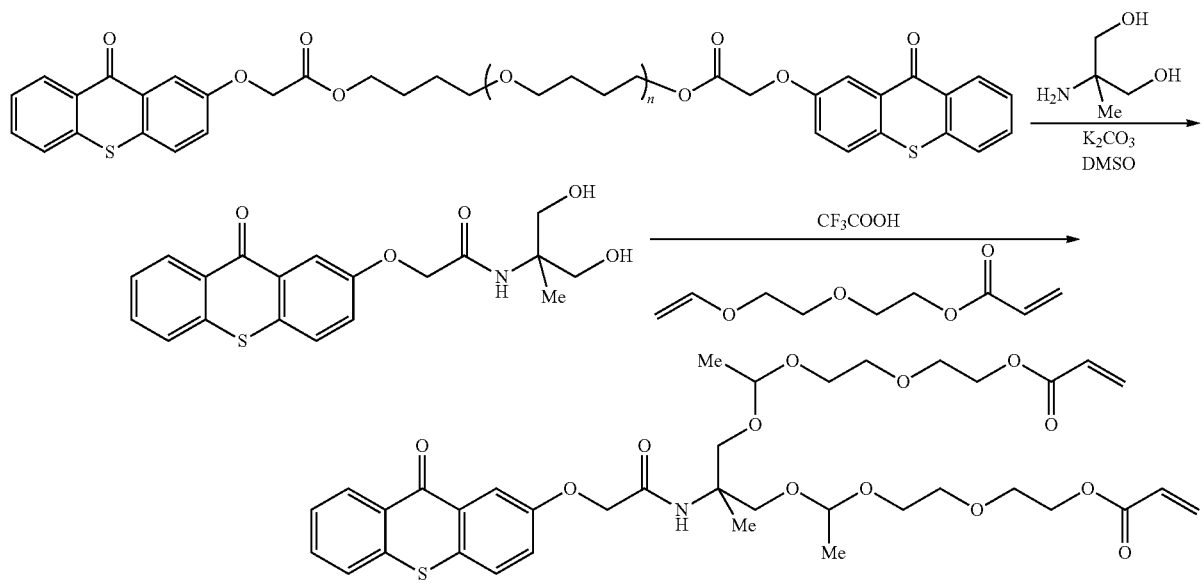

Step 1: The Aminolysis of Omnipol™ TX
30.96 g Omnipol™ TX was dissolved in 200 ml dimethyl sulfoxide. 21.4 g (0.155 mol) potassium carbonate was added and the reaction mixture was heated to 60° C. 16.3 g (0.155 mol) 2-amino-2-methyl-1,3-propane diol was added portion wise. The reaction was allowed to continue for one and a half hour at 60° C. The reaction mixture was allowed to cool down to room temperature. The precipitated salts were removed by filtration and washed with 30 ml acetone. The mixture was added to 160 ml water and the precipitated amido-dihydroxy-thioxanthone was isolated by filtration, washed with 160 ml acetone and dried. 23.5 g (81%) of the thioxanthone was isolated. (TLC-analysis: RP-C18 (Partisil™ KC18F, supplied by Whatman), eluent MeOH/0.5 M NaCl 80/20, $R_f$=0.36). TLC analysis showed the presence of a small amount of an isomeric structure ($R_f$=0.43). The following structure was assigned to the isomer:

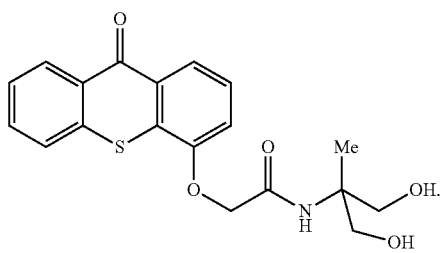 [SMILES: CC(CO)(CO)NC(=O)COc1cccc2c(=O)c3ccccc3sc12]

The intermediate was further used as a mixture of the main isomer and the minor isomer.

Step 2: The Addition to VEEA:

20 g (53 mmol) of the isolated amido-dihydroxy-thioxanthone was added to 148 g (0.796 mol) VEEA. 120 mg (79 µl, 1 mmol) trifluoroacetic acid and 220 mg (1 mmol) BHT were added and the reaction mixture was heated to 75° C. The reaction was allowed to continue for 16 hours at 75° C. The reaction was allowed to cool down to room temperature and 13 g of activated Lewatit M600 MB was added. The mixture was stirred for four hours at room temperature. The ion exchanger was removed by filtration. TX-2 was used as a solution in VEEA. (TLC-analysis: RP-C18 (Partisil™ KC18F, supplied by Whatman), eluent MeOH/0.5 M NaCl, $R_f$=0.25). Based on 1H-NMR analysis, the solution contained 21 wt % TX-2.

Example 1c

The Synthesis of Thioxanthone TX-11

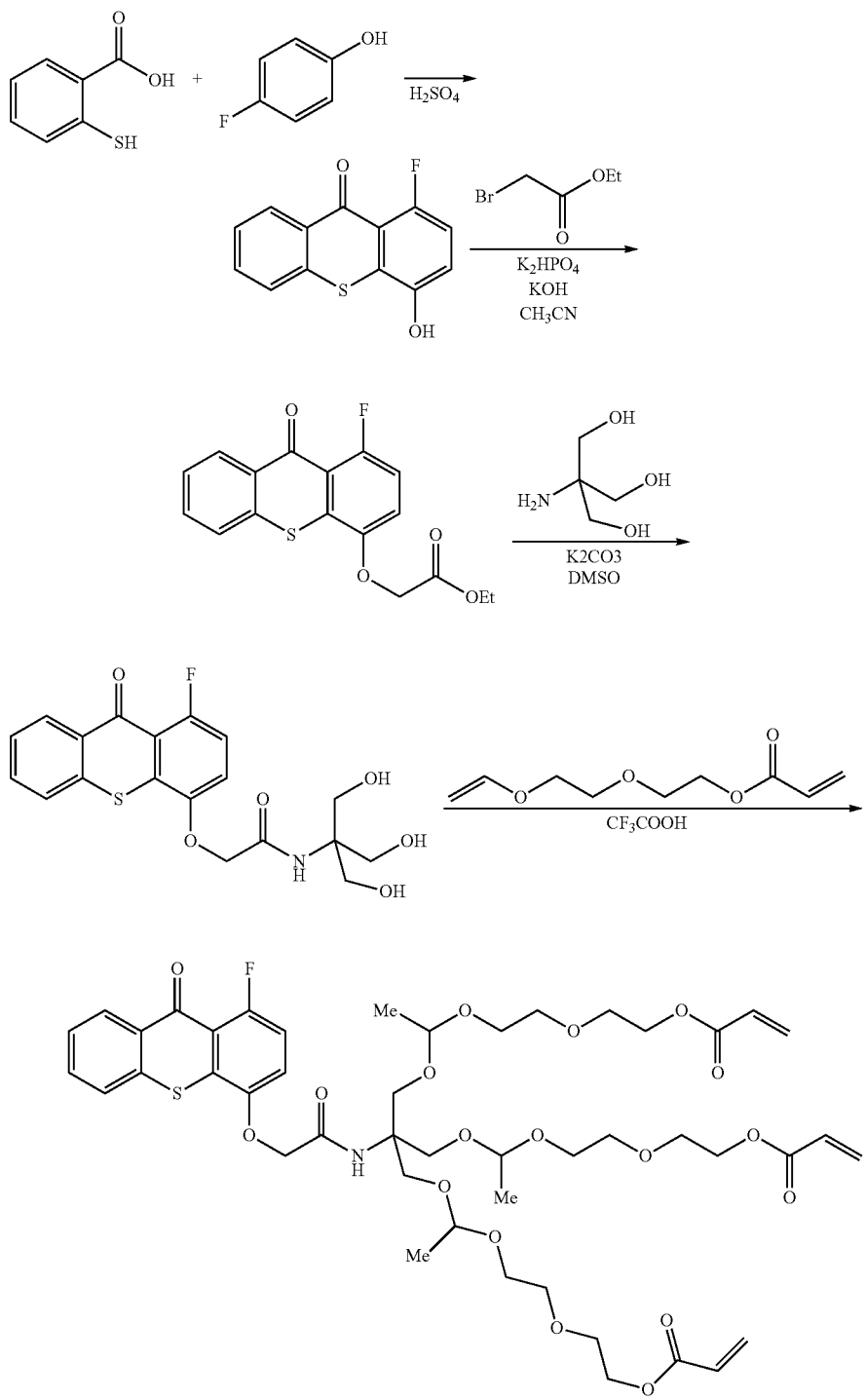

Step 1: The Synthesis of 1-fluoro-4-hydroxy-thioxanthen-9-one

Thiosalicylic acid (5.1 g, 0.033 mol) was added in portions to 20 mL sulfuric acid (18M), which causes the temperature to rise to 30° C. At this temperature 4-fluorophenol (11.2 g, 0.10 mol) was added in portions to the suspension. The mixture was heated to 80° C. and stirred for 12 hours. After the reaction, the reaction mixture was poured into ice (150 g). 1-fluoro-4-hydroxy-thioxanthen-9-one precipitated from the medium and was isolated by filtration. The crude 1-fluoro-4-hydroxy-thioxanthen-9-one was dissolved in water at pH=14 using an aqueous solution of potassium hydroxide and stirred for 60 minutes. The mixture was acidified to pH=4 using acetic acid. 1-fluoro-4-hydroxy-thioxanthen-9-one was isolated by filtration and dried to obtain 5.5 g of 1-fluoro-4-hydroxy-thioxanthen-9-one.

Step 2: The Alkylation of 1-fluoro-4-hydroxy-thioxanthen-9-one 3.5 g (20.3 mmol) dipotassium hydrogen phosphate was dissolved in 1.7 ml water. 10 ml acetonitrile was added and the mixture was heated to 60° C. 5 g (20.3 mmol) 1-fluoro-4-hydroxy-thioxanthen-9-one was added at 60° C., yielding a yellow orange dispersion. 5.2 ml (6.7 g, 40.6 mmol) bromoacetic acid ethyl ester was added dropwise. The mixture was stirred for five minutes and a solution of 2.3 g (40.6 mmol) potassium hydroxide in 10 ml water was added to adjust the pH to 12. The mixture was heated to 80° C. for 2 hours. The reaction mixture was allowed to cool down to room temperature and 30 ml water was added. The crude ester was isolated by filtration and treated with 20 ml acetonitrile. The thioxanthone ester was isolated by filtration and dried. 4.4 g (69%) of the intermediate ester was isolated (TLC-analysis: RP-C18 (Partisil™ KC18F, supplied by Whatman), eluent MeOH/0.5 M NaCl 8/2, $R_f$=0.42)

Step 3: The Aminolysis 4 g (12 mmol) of the thioxanthone ester, isolated in step 2, and 3.3 g (24 mmol) potassium carbonate were added to 50 ml dimethyl sulfoxide. The mixture was heated to 60° C. and 2.9 g (24 mmol) tris(hydroxymethyl)aminomethane was added and the reaction was allowed to continue at 60° C. for 1 hour. The reaction was allowed to cool down to room temperature. The residual salts were removed by filtration and washed with 10 ml acetone. The reaction mixture was added to 100 ml water. The tris-hydroxyamido-thioxanthone precipitated, was isolated by filtration and dried. 4.9 g (86%) of the amidothioxanthone was isolated (TLC analysis: RP-C18 (Partisil™ KC18F, supplied by Whatman), eluent MeOH/0.5 M NaCl 8/2, $R_f$=0.68)

Step 4: The Addition to VEEA 4.2 g (10 mmol) of the intermediate tris-hydroxyamido-thioxanthone was added to 39 g VEEA. 0.22 g (15 µl, 0.2 mmol) trifluoroacetic acid and 44 mg (0.2 mmol) BHT were added. The mixture was heated to 75° C. and the reaction was allowed to continue at 75° C. for 8 hours. The reaction mixture was allowed to cool down to room temperature and stirred over night at room temperature. 3.2 g of the activated Lewatit M600 MB was added. The mixture was stirred at room temperature for 2 hours. The ion exchanger was removed by filtration and TX-11 was used as solution in VEEA. (TLC-analysis: RP-C18 (Partisil™ KC18F, supplied by Whatman), eluent MeOH/0.5 M NaCl 8/2, $R_f$=0.1).Based on TH-NMR analysis, the solution was a 22 wt % solution of TX-11 in VEEA.

Example 2

This example illustrates the photoreactivity and the migration performance of polymerizable thioxanthones according to preferred embodiments of the present invention in comparison with state of the art polymerizable thioxanthones.

Preparation of Radiation Curable Compositions

The inventive and comparative radiation curable compositions INV-1 to INV-3 and COMP-1 were prepared according to Table 7. The weight percentage (wt %) was based on the total weight of the radiation curable compositions.

TABLE 7

| wt % of | COMP-1 | INV-1 | INV-2 | INV-3 |
|---|---|---|---|---|
| C-DISP | 16.0 | 16.0 | 16.0 | 16.0 |
| COMPTX-1 | 47.0 | — | — | — |
| TX-1 | — | 59.5 | — | — |
| TX-2 | — | — | 46.0 | — |
| TX-11 | — | — | — | 58.0 |
| IC819 | 2.5 | 2.5 | 2.5 | 2.5 |
| SC7040 | 1.2 | 1.2 | 1.2 | 1.2 |
| Omnipol ™ 910 | 2.5 | 2.5 | 2.5 | 2.5 |
| VEEA | 29.0 | 16.5 | 30.0 | 18.0 |
| Stabi-1 | 0.8 | 0.8 | 0.8 | 0.8 |
| UV3510 | 1.0 | 1.0 | 1.0 | 1.0 |

Results and Evaluation

The curing speed and the viscosity of the inventive radiation curable compositions INV-1 to INV-3 and the comparative radiation curable composition COMP-1 were determined. The results are given below in Table 8.

TABLE 8

| Radiation Curable Composition | Curing speed (% of the maximum output of the lamp) | Viscosity (mPa · s) |
|---|---|---|
| COMP-1 | 85 | 6.9 |
| INV-1 | 75 | 6.5 |
| INV-2 | 70 | 7.1 |
| INV-3 | 70 | 7.1 |

From Table 8, it becomes apparent that the radiation curable compositions according to preferred embodiments of the present invention yield highly reactive and jettable radiation curable formulations.

Evaluation of Migration Performance:

The inventive radiation curable compositions INV-1 to INV-3 and the comparative radiation curable composition COMP-1 were coated on a PET100 substrate using a bar coater and a 10 µm wired bar. All coated samples were cured were cured using a Fusion DRSE-120 conveyor, equipped with a Fusion VPS/1600 lamp (D-bulb). The samples were cured using a belt speed of 70 m/min and at full power of the lamp. Each sample was passed twice under the lamp.

Two samples of 7.068 cm$^2$ of COMP-1 and INV-1 to INV-3 were put into a 50 ml beaker and extracted with 4.5 ml acetonitrile, using ultrasound for 30 minutes. The extract was transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.45 µm filter. 15 µl of each sample was injected on the HPLC.

The chromatographic method used an Alltime™ C18.5 µm column (150 x 3.2 mm), supplied by Alltech, was used. A flow rate of 0.5 ml/min was used at a temperature of 40° C. The concentration of the different thioxanthones was determined relative to standard solutions at 312 nm.

The gradient with water as Eluent A and acetonitrile as Eluent B used for the determination of the thioxanthones is given in Table 9.

TABLE 9

| Time | % eluent A | % eluent B |
| --- | --- | --- |
| 0 | 55 | 45 |
| 6 | 55 | 45 |
| 11 | 0 | 100 |
| 30 | 0 | 100 |
| 31 | 55 | 45 |
| 38 | 55 | 45 |

The results are summarized in Table 10. The results are expressed as food ppb and calculated as follows. The amount of thioxanthone photoinitiator extractable from 14.136 cm$^2$ of each sample is calculated from the analysis and expressed in µg. This is recalculated to 6 dm$^2$, which corresponds to the surface area of a box containing one liter of a simulant. The recalculated amount of thioxanthone photoinitiator, expressed in µg corresponds to the amount that would have been extracted from the total surface area of the box in contact with one liter of the simulant. If the simulant would have a density of one, the extracted amount would correspond to the total amount of thioxanthone photoinitiator expressed as µg in one kilogram of simulant or ppb.

TABLE 10

| Radiation curable composition | Thioxanthone photoinitiator Type | food ppb |
| --- | --- | --- |
| COMP-1 | COMPTX-1 | 268 |
| INV-1 | TX-1 | 119 |
| INV-2 | TX-2 | 256 |
| INV-3 | TX-11 | 88 |

From Table 10, it becomes apparent that the radiation curable compositions comprising a thioxanthone according to preferred embodiments of the present invention lead to low amounts of extractables.

Example 3

This example illustrates the improvement of the thermal stability of a CMYK inkjet ink set wherein the inkjet inks included a polymerizable thioxanthone photoinitiator in accordance with the present invention compared to a state of the art polymerizable thioxanthone.

Preparation of Radiation Curable Compositions

A comparative inkjet ink set COMP-CMYK was prepared according to Table 11.

TABLE 11

| wt % of | COMP-CMYK | | | |
| --- | --- | --- | --- | --- |
| | COMP-C | COMP-M | COMP-Y | COMP-K |
| COMPTX-1SOL | 19.1 | 16.0 | 16.0 | 19.1 |
| Type-I | 16.6 | 13.3 | 13.3 | 16.6 |
| SC7040 | 3.7 | 1.2 | 1.2 | 1.2 |
| IC819 | 5.0 | 5.0 | 5.0 | 2.5 |
| C-DISP | 16.0 | — | — | 2.7 |
| M-DISP | — | 15.3 | — | 2.7 |
| Y-DISP | — | — | 18.0 | — |
| K-DISP | — | — | — | 15.3 |
| VEEA | 37.8 | 47.4 | 44.7 | 38.1 |
| UV3510 | 1.0 | 1.0 | 1.0 | 1.0 |
| Stabi-1 | 0.8 | 0.8 | 0.8 | 0.8 |

An inventive inkjet ink set INV-CMYK was prepared according to Table 12 in the same manner as the comparative inkjet ink set COMP-CMYK by replacing the polymerizable thioxanthone photoinitiator COMPTX-1 by the polymerizable thioxanthone photoinitiator TX-1. TX-1 was used in a more concentrated solution as disclosed in Example 1. The final solution had a concentration of 47 wt % and was prepared as follows. A mixture of 108.74 g (0.280 mol) of the starting amidothioxanthone, as disclosed in example 1, 420.98 g VEEA and 1.23 BHT was heated to 75° C. 7.98 g crosslinked poly(vinylpyridinium) tosylate was added and the reaction was allowed to continue for 22 hours at 75° C. The reaction mixture was allowed to cool down to room temperature and the catalyst was removed by filtration, together with a small residue of starting material. The solution was used as such in the inventive ink set. The concentration of TX-1 was determined based on $^1$H-NMR analysis of the solution. The TX-1 concentration was 47.2% by weight. The COMPTX-1 concentration in COMPTX-1SOL was 43% by weight.

TABLE 12

| wt % of | INV-CMYK | | | |
| --- | --- | --- | --- | --- |
| | INV-C | INV-M | INV-Y | INV-K |
| TX-1SOL | 24.0 | 19.8 | 19.8 | 24.0 |
| Type-I | 16.6 | 13.3 | 13.3 | 16.6 |
| SC7040 | 3.7 | 1.2 | 1.2 | 1.2 |
| IC819 | 5.0 | 5.0 | 5.0 | 2.5 |
| C-DISP | 16.0 | — | — | 2.7 |
| M-DISP | — | 15.3 | — | 2.7 |
| Y-DISP | — | — | 18.0 | — |
| K-DISP | — | — | — | 15.3 |
| VEEA | 32.9 | 43.6 | 41.0 | 33.2 |
| UV3510 | 1.0 | 1.0 | 1.0 | 1.0 |
| Stabi-1 | 0.8 | 0.8 | 0.8 | 0.8 |

The curing speed of both ink sets COMP-CMYK and INV-CMYK was evaluated as follows. Three samples of the comparative inks COMP-1 to COMP-4 and the inventive inks INK-1 to INV-4 were coated on a PET100 substrate using a bar coater and a 10 µm wired bar. All coated samples were cured were cured using a Fusion DRSE-120 conveyor, equipped with a Fusion VPS/1600 lamp (D-bulb). The first sample of each ink was cured at a belt speed of 20 m/min. The percentage of the maximum output of the lamp was used as a measure for the curing speed. The lower the number the higher the curing speed. A second sample of each ink was cured using a belt speed of 50 m/min. A third sample of each ink was cured, using a belt speed of 70 m/min. A number above 100 means that a second pass was required. The percentage used in the second pass is added to the 100% used in the first pass, leading to a number above 100. The results are summarized in Table 13.

TABLE 13

| Radiation curable inkjet ink | Curing speed | | |
| --- | --- | --- | --- |
| | 20 m/min | 50 m/min | 70 m/min |
| INV-C | 50 | 70 | 100 |
| COMP-C | 50 | 70 | 100 |
| INV-M | 55 | 75 | 100 |
| COMP-M | 55 | 75 | 100 |
| INV-Y | 50 | 75 | 90 |
| COMP-Y | 50 | 75 | 90 |
| INV-K | 80 | 150 | 200 |
| COMP-K | 90 | 150 | 200 |

From Table 13, it becomes apparent that the different inventive inks in the ink set INV-CMYK are at least as sensitive as the comparative inks in the comparative ink set INV-CMYK. Therefore, the relative thermal stability of the inventive and comparative ink set can be compared.

The inks of both ink sets were stored for 7 days at 80° C., shielded from light. The viscosity was measured a Brookfield DV-II+ viscometer at 40° C. at 12 rotations per minute (which corresponds to a shear rate of 90 s$^{-1}$). The results of the initial viscosity and the relative increase in viscosity are summarized in Table 14.

TABLE 14

| Radiation curable inkjet ink | Initial viscosity (mPa · s) | Relative increase in viscosity |
|---|---|---|
| INV-C | 10.5 | 4% |
| COMP-C | 9.9 | 40% |
| INV-M | 9.1 | 0% |
| COMP-M | 8.6 | 0% |
| INV-Y | 8.7 | 15% |
| COMP-Y | 8.3 | 27% |
| INV-K | 9.8 | 2% |
| COMP-K | 8.0 | 15% |

From Table 14, it becomes apparent that on average the inks of the comparative ink set COMP-CMYK exhibited a relative increase in viscosity of 21%, while the inks of the inventive ink set INV-CMYK only increased by 5% on average in viscosity.

The invention claimed is:

1. A polymerizable thioxanthone according to Formula (I):

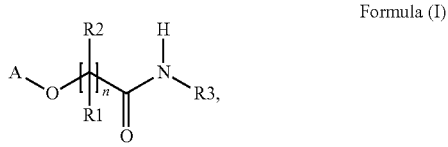

Formula (I)

wherein
A represents a thioxanthone moiety;
R1 and R2 are independently selected from the group consisting of a hydrogen, an alkyl group, an alkenyl group, an alkynyl group, an aryl group, and a heteroaryl group;
n represents 1 or 2; and
R3 represents a moiety including at least one free radical polymerizable group selected from the group consisting of an acrylate, a methacrylate, an acrylamide, a methacrylamide, a styrene group, a maleate, a fumarate, an itaconate, a vinyl ether, a vinyl ester, an allyl ether, and an allyl ester.

2. The polymerizable thioxanthone according to claim 1, wherein A represents a thioxanthone moiety substituted in a 1-position by a halogen, an alkyl group, or an alkoxy group.

3. The polymerizable thioxanthone according to claim 2, wherein Formula (I) has a structure according to Formula (II) or Formula (III):

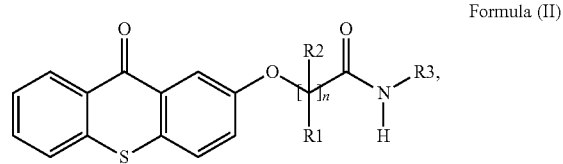

Formula (II)

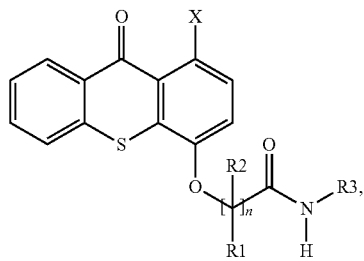

Formula (III)

wherein X is selected from the group consisting of a hydrogen, a halogen, an alkyl group, and an alkoxy group.

4. The polymerizable thioxanthone according to claim 3, wherein X represents a fluorine.

5. The polymerizable thioxanthone according to claim 1, wherein R1 and R2 are independently selected from the group consisting of hydrogen and an alkyl group having 1 to 6 carbon atoms.

6. The polymerizable thioxanthone according to claim 5, wherein R1 and R2 are both hydrogen.

7. The polymerizable thioxanthone according to claim 1, wherein the at least one free radical polymerizable group is selected from the group consisting of an acrylate and a methacrylate.

8. The polymerizable thioxanthone according to claim 1, wherein the moiety R3 includes two or three free radical polymerizable groups.

9. The polymerizable thioxanthone according to claim 8, wherein the two or three free radical polymerizable groups are independently selected from the group consisting of an acrylate and a methacrylate.

10. The polymerizable thioxanthone according to claim 1, wherein n is equal to 1.

11. The polymerizable thioxanthone according to claim 3, wherein n is equal to 1.

12. A radiation curable composition including the polymerizable thioxanthone according to claim 1.

13. A radiation curable composition including the polymerizable thioxanthone according to claim 7.

14. The radiation curable composition according to claim 12, further comprising a monomer according to Formula (IV):

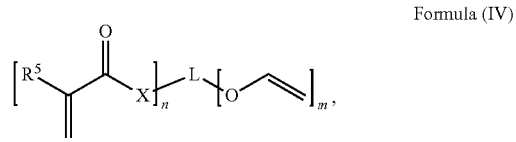

Formula (IV)

wherein
L represents a linking group;
m and n independently represent an integer having a value from 1 to 5;
X represents O, S, or NR$^6$; and
R$^5$ and R$^6$ independently represent hydrogen or a substituted or unsubstituted alkyl group;
with the proviso that when X =NR$^6$ then L and R$^6$ may together form a ring system.

15. The radiation curable composition according to claim 12, wherein the radiation curable composition is an inkjet ink having a viscosity smaller than 15 mPa·s at 40° C. and at a shear rate of 1,000 s$^{-1}$.

16. A substrate including a cured layer of the radiation curable composition according to claim 12.

17. A method of inkjet printing, the method including the step of:
   jetting the radiation curable composition of claim 12 onto a substrate.

* * * * *